United States Patent [19]
Wang et al.

[11] Patent Number: 5,676,820
[45] Date of Patent: Oct. 14, 1997

[54] REMOTE ELECTROCHEMICAL SENSOR

[75] Inventors: Joseph Wang, Las Cruces, N. Mex.; Khris Olsen, Richland, Wash.; David Larson, Las Cruces, N. Mex.

[73] Assignee: New Mexico State University Technology Transfer Corp., Las Cruces, N. Mex.

[21] Appl. No.: 383,717

[22] Filed: Feb. 3, 1995

[51] Int. Cl.$^6$ .................................................. G01N 27/26
[52] U.S. Cl. ........................ 205/777.5; 205/776.5; 205/792; 205/793.5; 205/787; 204/403; 204/406; 204/412; 204/413; 204/434; 435/817
[58] Field of Search ................................ 204/403, 406, 204/412, 413, 434, 153.1, 153.12, 404; 435/817; 205/775, 776.5, 777.5, 792, 793.5, 787

[56] References Cited

U.S. PATENT DOCUMENTS

| | | |
|---|---|---|
| 1,707,291 | 4/1929 | Waite et al. |
| 3,094,692 | 6/1963 | Westneat, Jr. et al. ............... 340/345 |
| 3,259,568 | 7/1966 | Jordan et al. ............... 210/28 |
| 3,410,793 | 11/1968 | Stranahan et al. ............... 208/159 |
| 3,855,099 | 12/1974 | Matson ............... 204/195 F |
| 3,904,487 | 9/1975 | Lieberman et al. ............... 204/1 T |
| 3,943,488 | 3/1976 | Kazahaya ............... 340/147 C |
| 3,948,681 | 4/1976 | Barger, Jr. et al. ............... 136/86 D |
| 4,003,705 | 1/1977 | Buzza et al. ............... 23/230 R |
| 4,058,446 | 11/1977 | Zirino et al. ............... 204/195 R |
| 4,077,030 | 2/1978 | Helava ............... 340/183 |
| 4,090,926 | 5/1978 | Matson ............... 204/11 |
| 4,201,646 | 5/1980 | Matson ............... 204/195 H |
| 4,327,166 | 4/1982 | Leger ............... 429/194 |
| 4,374,041 | 2/1983 | Matson ............... 436/60 |
| 4,524,354 | 6/1985 | Morgan ............... 340/825.36 |
| 4,545,382 | 10/1985 | Higgins et al. ............... 128/635 |
| 4,568,935 | 2/1986 | Phillips et al. ............... 340/825.05 |
| 4,586,136 | 4/1986 | Lewis ............... 364/418 |
| 4,601,886 | 7/1986 | Hudgins ............... 422/116 |
| 4,622,276 | 11/1986 | Walsh ............... 429/46 |
| 4,626,992 | 12/1986 | Greaves et al. ............... 364/418 |
| 4,628,315 | 12/1986 | Douglas ............... 340/870.26 |
| 4,661,210 | 4/1987 | Tenygl ............... 204/1 T |
| 4,695,555 | 9/1987 | O'Keeffe ............... 436/150 |
| 4,783,748 | 11/1988 | Swarztrauber et al. ............... 364/483 |
| 4,786,373 | 11/1988 | Saloheimo et al. ............... 204/1 T |
| 4,804,443 | 2/1989 | Newman et al. ............... 204/1 T |
| 4,831,558 | 5/1989 | Shoup et al. ............... 364/550 |
| 4,865,992 | 9/1989 | Hach et al. ............... 436/51 |
| 4,888,295 | 12/1989 | Zaromb et al. ............... 436/161 |
| 5,019,515 | 5/1991 | Gisin et al. ............... 436/52 |
| 5,045,214 | 9/1991 | Walker ............... 210/717 |
| 5,091,299 | 2/1992 | Turner et al. ............... 204/403 |
| 5,120,421 | 6/1992 | Glass et al. ............... 204/406 |

(List continued on next page.)

FOREIGN PATENT DOCUMENTS

| | | |
|---|---|---|
| 0 569 908 A2 | 11/1993 | European Pat. Off. |
| 1 505 553 | 3/1978 | United Kingdom. |
| WO 89/09388 | 10/1989 | WIPO. |
| WO 91/08474 | 6/1991 | WIPO. |
| WO 92/18857 | 10/1992 | WIPO. |

OTHER PUBLICATIONS

Adam, K., "Field Method for Determination of Suface Contamination Density," *Int'l Conf on Nuclear Spectroscopy and Nuclear Structure*, (16–19 Apr. 1991).

(List continued on next page.)

*Primary Examiner*—Bruce F. Bell
*Attorney, Agent, or Firm*—Deborah A. Peacock; Paul Adams

[57] ABSTRACT

An electrochemical sensor for remote detection, particularly useful for metal contaminants and organic or other compounds. The sensor circumvents technical difficulties that previously prevented in-situ remote operations. The microelectrode, connected to a long communications cable, allows convenient measurements of the element or compound at timed and frequent intervals and instrument/sample distances of ten feet to more than 100 feet. The sensor is useful for both downhole groundwater monitoring and in-situ water (e.g., shipboard seawater) analysis.

24 Claims, 12 Drawing Sheets

U.S. PATENT DOCUMENTS

| | | | |
|---|---|---|---|
| 5,131,999 | 7/1992 | Gunasingham | 204/411 |
| 5,191,327 | 3/1993 | Talmadge et al. | 340/870.38 |
| 5,192,409 | 3/1993 | Wang et al. | 204/409 |
| 5,237,031 | 8/1993 | Kubota et al. | 526/305 |
| 5,254,235 | 10/1993 | Wu | 204/284 |
| 5,292,423 | 3/1994 | Wang | 204/434 |
| 5,296,125 | 3/1994 | Glass et al. | 204/153.21 |
| 5,298,129 | 3/1994 | Eliash | 204/434 |
| 5,333,114 | 7/1994 | Warrior et al. | 364/550 |
| 5,366,634 | 11/1994 | Vijayan et al. | 210/638 |
| 5,389,215 | 2/1995 | Horiuchi et al. | 204/153.1 |
| 5,422,014 | 6/1995 | Allen et al. | 210/743 |
| 5,437,772 | 8/1995 | DeCastro et al. | 204/406 |
| 5,512,489 | 4/1996 | Girault et al. | 205/792 |

OTHER PUBLICATIONS

Aldstadt, J.H., "Determination of Heavy Metals by Thin–Layer Chromatography–Square–Wave Anodic Stripping Volta.", *Anal. Chem.* vol.. 64, pp. 3176–3179 (1992) no month available.

Analytical Chemistry, "Blood Lead Measurement Takes the Direct Approach," *Analytical Chem.*, vol. 65, No. 5, p. 265A (Mar. 1, 1993).

Arnold, M.A., "Fiber–Optic Chemical Sensors," *Anal Chem*, vol. 64, No. 21, p. 1015A, Abstract Only, (Nov. 1, 1992).

Asher, J.C., "Experience of Plant Corrosion Monitoring by Thin Layer Activation," *Proc of Tech Symp of Corrosion '86*, Abstact Only, Houston TX USA (17 Mar. 1986).

Atomic Energy of Canada Ltd., "Progress Report, Health Sciences Div., Chalk River Nuclear Labs", Abstract Only, (Nov. 1980).

Auxier, J.A., et al., "Industrial Safety and Applied Health Physics Div Annual Report for–1981," Oak Ridge National Lab, TN (USA) (Abstract Only) (Aug. 1982).

Balogh, K., "comparison of Mussels and Crustacean Plankton to Monitor Heavy Metal Pollution," *Balaton Limnological Res. Inst., Hungarian Acad. Sci.*, Tihany, Hungary, vol. 37, No. 3–4, pp. 281–292 Abstract Only) 1988 no month available.

Bastiaans, G.J., et al., "Chemical Sensors Technology Development Planning Workshop," *Ames Lab.*, (Abstract Only) (Mar. 1993).

Birge, W.J., "Embryo–Larval Bioassays on Inorganic Coal Elements and in situ Biomonitoring of Coal–Waste Affluents," *Univ of Kentucky., Lexington USA,* (Abstract Only), (3 Dec. 1978).

Bonakdar, J.L., "Bioamperometric Sensors for Phenol Based on Carbon Paste Electrodes," *J. Electroanal. Chem.*, vol. 266 pp. 47–55,(1989) (Abstract Only) no month available.

Bueker, H., et al., "Elcobox I", *Nuclear Research center, Juelich,* Ann. Meeting of Inst. of Nuclear Materials Management, Albuq NM USA (Abstract Only) (21 Jul. 1985).

Campanella, L., et al., "Determination of Phynol in Wastes and Water Using an Enzyme Sensor," *Analyst*, vol. 118, (Abstract Only), (Aug. 1993).

Cervinka, J., et al., "Equipment for Monitoring Process of Burning of Water or Water Vapor in Liquid Sodium, and of Material Entrainment Due to this Burning," (Abstract Only) (Feb. 1, 1983).

Chan, S.S., et al., "In Situ Laser Raman Spectroscopy: Comparison", *Pittsburgh Conf and Exp. on Analytical Chem and Applied Spectroscopy*, Atlantic City NJ USA, 9Abstract Only (10 Mar. 1986).

Chudyk, W.A., "Remote Detection of Groudwater Contaminants Using Far–Ultraviolet Laser–Induced Fluorescence," *Anal. Chem.*, vol. 57, No. 7, pp. 1237–1342 (Jun. 1985).

Cole–Palmer, Advertisement "Oakton ElectraScan EC–1 Series", brochure (Feb. 1991).

D'Silva, A.P., et al., "Remote, Real–time Analysis of Hazardous Wastes Through Laser Ablation–inductively Coupled Plasma Atomic Emission Spectrometry," *Proc. of the Information Exchange Meeting on Characterization, Sensors and Monitoring Technologies,* US DOE/Dallas TX (USA) (Abstract Only) 15–16 Jul. 1992).

Daniels, J.I., et al., "Evaluation of Military Field–Water Quality," *Final Report, vol. 9, Data for Assessing Health Risks in Potential Theaters of Operation for US Military Forces,* Lawrence Livermore National Lab CA (USA) (Abstract Only) (Feb. 1988).

Davy, D.R., "Freshwater Mussel, Velesunio Angasi—a Monitor for Radium–226 Pollution in the Alligator Rivers Region, Northern Territory," *Australian Atomic Energy Comm. Research Est., Lucas Heights,* Darwin, North Territory, Australia (Abstract Only) (9 Jul. 1984).

Dotson, D.W., et al., "In–Situ Tritium Borehole Probe for Measurement of Tritium," U.S. 4,464,338, Dept of Interior filed 24 Oct. 1980, (7 Aug. 1984). (Abstract Only).

Duray, J.R., Et al., "Nonintrusive and Intrusive Sensing of Environmentally Important Objects," *Proc of the Information Exchange Meeting on Characterization, Sensors and Monitoring Technologies,* US DOE, Information Exchange Meeting Dallas TX (USA) (Abstract Only), (15–16 Jul. 1992).

Durler, D.L. et al., "In–Situ Uranium Leach Mining: Considerations for Monitor Well Systms," *U.S. Steel Corp. Soc. of Petr Eng,* Dallas TX USA (Abstract Only) (21 Sep. 1980).

Derwent Publ., WPI 75–60813W/37; Patent assignee, Environm Sci Assoc. (Abstract Only) no month or year available.

Edlund, David, et al., "Thin–Film Polymetric Sensors for Detection and Quantification of Multivalent Metal Ions," *Bend Research, Inc.,* Bend Ore USA, *Sensors and Actuators,* vol. B10 (Abstract Only) (3 Feb. 1993), pp. 185–190.

Euromar Project "Mermaid", Bonn Germany (Abstract Only) (Mar. 1991).

Fischer, K.P., et al., "Field Testing of Deep Water Cathodic Protection on the Norwegian Continental Shelf," *Norwegian Marine Technology Res. Inst.,* (Abstract Only) (Jan. 1988).

Gil, E.P., et al., "Potentiometric Stripping Determination of Mercury (II), Selenium (IV), Copper (II) and Lead (II) at a Gold Film Electrode in Water Samples," *Analytica Chimica Acta,* vol. 293, pp. 55–65 (1994) Abstract Only no month available.

Gogolak, C.V., et at., "Survey of Gamma Radiation in the Vicinity of the Asse Saltmine Radioactive Waste Disposal Site," *Bundesgesundheisamt, Neuherberg (German, F>R>) Inst. Fuer Strahlenhygiene* (Abstract Only) (Sep. 1981).

Green, Monika, et al., "Disposable Single–Use Sensors," (Abstract Only) *Analytical Proceedings,* vol. 28, p. 374 (Nov. 1991).

Grigor'ev, A.I., et al., "Instrumental Neutron–Activation Analysis of Oceanic Nodules on a Unit Containing a Radionuclide Neutron Source," (Abstract Only) *Institute of Chemistry, Vladivostok USSR; J. Anal. Chem USSR,* vol. 41, No. 6 pp. 792–796 no month or year available.

Hamburg Univ (Germany), "Circulation and Pollutant Turnover in the North Sea, final report," (Abstract Only) *Bundesminiserium fuer Forschung and Technologie,* Bonn (Germany) No. T 2351 193p. (Apr. 1990).

Harasawa, SH, et al., "Monitoring of Neutron Fluenee Rate by Capture Gamma Rays for Boron Neutron Capture Therapy," *Proceedigns of First Asian Syposium on Research Reactors*, pp. 291–296 (Abstract Only) (18 Nov. 1986).

Hearn, R.A., et al., "Remote Measurement of Collant and Effluent Parameters in Operating Nuclear Power Plants," *IEEE Trans. Nucl. Sci.*, vol. 30, No. 1 (Feb. 1983) (Abstract Only).

Hearst, J.R., et al., "In–Situ Equivalent CO sub 2 Estimates Using a Neutron–Induced Gamma–ray Spectroscopy Logging System," *Symposium on Containment of Underground Nuclear Explosions*, Santa Barbara CA pp. 160–186 (19–21 Sep. 1989) (Abstract only).

Hilditch, P.I., et al., "Disposable Electrochemical Biosensors," *Analyst*, p. 1217 (Dec. 1991) (Abstract Only).

Hilton, J., et al., "Monitoring in the Vadose Zone at Two Inactive Uranium Mill Tailings Sites," *Geotechnical and Geophdrytogical Aspects of Waste Management Symposium*, pp. 439–446 (5 Feb. 1986) (Abstract Only).

Hilton, E.R., Jr., et al., "Development of an On–Line Mercury Stream Monitor," *Environ. Sci. Technol.*, vol. 21, No. 2, pp. 198–202 (Feb. 1987) (Abstract Only).

Hopkins, W.C., "Three Mile Island Unit 2: The Early Radiological Conditions of the Reactor Building," *Joint Meeting of European Nuclear Soc and Amer Nuclear Soc.*, Trans.Am Nucl. Soc. vol. 57, pp. 447–449 (30 Oct.–4 Nov. 1988) (Abstract Only).

Huiliang, H., et al., "Carbon Fiber Electrodes in Flow Potentiometric Stripping Analysis", *Analytica Chimica Acta*, vol. 193, pp. 61–69 (1987) no month available.

Indig, M.E., "In Situ Electrochemical Measurements in BWRs", *Proc: 1989 Workshop on LWR Radation Water Chemistry and its Influence on In–Care Structural Materials*, (14–15 Nov. 1989) (Abstract Only).

Instrument Soc of America, "International European Region Conference on Environmental Protection, Control and Monitoring," *Instrument Society of America*, 104 p (1991) (Abstract Only) no month available.

Janata, J., "Potentiometric Gas Sensors Based on Field Effect Transistors", *Pittsburgh Conf and Exp on Analytical Chem and Applied Spec.*, (1987) (Abstract Only) no month available.

Journal of Animal Production Research, "Physiological Variations in Snails Bulinus–Phyopsis–Globosus in . . . Nigeria," *J. Anim Prod. Res*, vol. 9, No. 1–2, pp. 43–52 (1989) (Abstract Only) no month available.

Keeny, W.L., et al., "Determination of Trace Metals in Cladophora Glomerata: C Glomerata as a Potential Biological Monitor," *Water Res.* vol. 10, No. 11 pp. 981–984 (1976) (Abstract Only) no month available.

Klainer, S., et al., "Monitor for Detecting Nuclear Waste Leakage in a Subsurface Repository," *Lawrence Berkeley Lab., CA (USA)*, (5 Nov. 1980) (Abstract Only).

Klatt, L.N., et al., "Fiber Optic Sensors for the Study of Falling Liquid Films," *Symp. on Chem. Sensors and Microinstrumentation*, 120 p. (25–30 Sep. 1988) (Abstract Only).

Koryta, J., (ed.), "Ions, Electrodes and Membranes, 2nd Ed.", Wiley & Sons, NYC NY (1991) (Review Only) no month available.

Kovalevwskii, A.L., et at, "Determination of Zinc in Tree Crust by Field X–Ray Analyzers," *Dokl. Akad. Nauk SSSR (USSR)*, vol. 251, No. 1, pp. 173–175 (1980) (Abstract Only) no month available.

Kramar, U.J., et al., "Application of Energy Dispersive X–Ray Fluorenscence, Ion–Sensative Electrode and Instrumental Neutron Aactivation in Geochemical Prospecting," *Bundesministerium fuer Forschung und Technologie, Bonn* (Germany), (1982) (Abstract Only) no month available.

Kubiak, W.W., "Anodic–StrippingVoltammetry of Heavy Metals in the Presence of Organic Surfactants," *Talanta*, vol. 36, No. 8, pp. 821–824 (1989) no month available.

Kueppers, G., "Development of Activation Analytical Methods for the Determination of Trace Amount in Natural Wastes," *Technische Hochschule Aachen (Germany, F.R.)*, (27 Jan. 1981) (Abstract Only).

Leonard, P.H., "Implementation of a Field Portable–X–Ray Fluorescence System at the C C Battery Superfund Site," *Proc of Nat'l Research and Dev. Conf on Control of Hazardous Materials*, 549 p, pp. 523–525 (20–22 Feb. 1991) (Abstract Only).

Lerch, K., "Neurospora Tyrosinase: Structural, Spectroscopic and Catalytic Properties," *Molecular and Cellular Biochemistry*, vol. 42 pp. 125–138 (1983) no month available.

Levine, H.G., "Green Seaweed Ulva as a Monitor for Pollution in Coastal Waters," *Univ of MA Thesis*, 253 pp. (1983) (Abstract Only) no month available.

Lieberman, S.H., et al., "Fluorescence–Based Fiber Optic Chemical Sensors for Direct Determination of Trace–Transition Metals in Seawater," *Amer Geophysical Union 1988 Fall Meeting*, (1988) (Abstract Only) no month available.

MacCarthy, P., et al., "Water Analysis," *Anal. Chem.*, vol. 65, pp. 244R–292R (1993) no month available.

McLaughlin, K., et at., "Anodic Stripping Voltammetry of Selenium (IV) at a GoldFiber Working Electrode," *Eletroanalysis*, vol. 4 pp. 689–693 (1992) no month available.

Malito, M.L., "Ancillary Operations in Coal Preparation Instrumentation On–Line Law Cost Sulfur and Ash Analyzer," *Babcock and Wilcox Co.*, 343 p (Jul. 1991) (Abstract Only).

Manushev, B., et al., "In–Situ Gamma Spectroscopic Measurement of Natural Waters in Bulgaria," *Bulg. J. Phys.*, vol. 10, No. 4 pp. 411,415 (1983) (Abstract Only) no month available.

Mednikov, E.P., et al, "Remote Sampling of Radioactive Aerosols at Atomic Power Stations," *Sov. At. Energy.* Vol. 62, No. 1, pp. 49–62 (Jul. 1987) (Abstract Only).

Meyers–Schoene, L., "Comparison of Two Freshwater Turtle Species as Monitors of Environmental Contamination," *Univ of Tenn Thesis*, 163 p (Apr. 1990) (Abstract Only).

Micheletti, W.C., et al., "Cooling Water Treatment Field Testing for Scaling Control," *Electric Power Research Int.*, Proc of Amer Power Conf., vol. 46 pp. 954–959 (24 Apr. 1984) (Abstract Only).

Munakata, T., et al., "Fuzzy Systems: An Overview," *Communications of the ACM*, vol. 37, No. 3, pp. 69–84 (Mar. 1994).

Murphy, E.M., et al., "Evaluation of Chemical Sensors for In Situ Ground–Water Monitoring at the Hanford Site," *Pacific Northwest Lab. Richland WA (USA)*, Report PNL–6854 p. 85 (Mar. 1989) Abstract Only.

Nielsen, H.O., "Environment and Pollution Measurement Sensors and Systems," SPIE, 207 p (12–16 Mar. 1990) Abstract Only.

Oak Ridge National Lab TN (USA), "Industrial Safety and Applied Health Physics, Annual Report," 133 p (Nov. 1981) Abstract Only.

Olsen, K.B., et al., "On–Site Analysis of Metqals in Soils Using Stripping Voltammetry," *Conference: Information Exchange Meeting on Characterization Sensors*, p. 3, paper 30 (261 p) (Jul. 1992) Abstract only.

Ortega, F., et al, "Liquid Chromatographic Separation of Phenolic Drugs Using Catalytic Detection: Comparison of an Enzyme Reactor and Enzyme Electrode," *J of Pharm & Biomed Analysis*, vol. 10, Nos. 10–12 pp. 789–796 (1992) no month available.

Ortiz, A., "Advance in the Research and Use of Remote Sensors in Natural Resources Development Studies: Chile," *12th Intl Symp on Remote Sensing of Environment*, vol. 1, pp. 1583–1595 (1978) Abstract no month available.

Ostapczuk, P., "Present Potentials and Limitations in the Determination of Trace Elements by Potentiometric Stripping Analysis," *Analytica Chimica Acta*, pp. 35–40 (1993) no month available.

Pacific Northwest Lab, "Ground Water Monitoring Compliance Projects for Hanford Site Facilities," (Nov. 1987) Abstract Only.

Packer, T.W., "Determination of the Concentration of Uranium in Soil and Stream Sediment Samples Using a High Resolution Energy–Dispersive X–Ray Fluorescence Analyser," *Int. J. Appl. Radiat. Isot.*, vol. 34, No. 1, pp. 273–281 (Jan. 1983) Abstract Only.

Perone, S.P., et al., "Application of Mercury–Plated Graphite Electrodes to Voltammetry and Chronopotentiometry," *J Electroanal. Chem.*, vol. 12, pp. 269–276 (1966) no month available.

Perrin, M., "Plant Analyzers and Part Task Simulators," *Proc; 1988 Conf on Power Plant Simulators and Modeling*, 716 p (15–17 Jun. 1988 and Feb. 1990) Abstract Only.

Phillips, D.J.H., "Use of Biological Indicator Organisms to Monitor Trace Metal Pollution in Marine and Estuarine Environments: A Review," *Environ, Pollut.*, vol. 14, No. 4, pp. 281–317 (Aug. 1977) Abstract.

Piorek, S., et al., "A New Calibration Technique for X–Ray Analyzers Used in Hazardous Waste Screening," *Hazardous Wasts and Hazardous Materials, Conference*, pp. 428–433 (19–21 Apr. 1988) Abstract.

Radwanowski, L.J., "Equipment for Measuring Radiation," *Tech Poszukiwan Geol (Poland)*, pp. 30–37 (1979) Abstract no month available.

Ray, S.N., et al., "Equisetum Arvense—An Aquatic Vascular Plant as a Biological Monitor for Heavy metal Pollution," *Chemophere (UK)*, vol. 8, No. 3, pp. 125–128 (1979) no month available.

Rasmussen, L., et al., "Soil Water Samplers in Ion Balance Studies on Acidic Forest Soils," *Bull. Environ. Contam. Toxicol*, vol. 36, No. 4 pp. 563–570 (Apr. 1986) Abstract.

Rivas, G., et al., "Electrochemical Determination of the Kinetic Parameters of Mushroom Tyrosinase," *Bioelectrochemistry and Bioenergetics*, vol. 29, pp. 19–28 (1992) Abstract no month available.

Robertiello, A., et al., "Nickel and Vanadium as Biodegradation Monitors of Oil Pollutanats in Aquatic Environments," *Water Res. (UK)*, vol. 17, No. 15, pp. 497–500 (1983) Abstract no month available.

Schiager, K.J., et al., "Simple Field Method for Determining Compliance with EPA Land Cleanup Standards", *Ann, Symp on Uranium Mill Tailings Management*, pp. 135–148 (9 Dec. 1982) Abstract.

Semonin, R.G., "Study of Air Pollution Scavenging," *14th Progress Report, Illinois State Water Survey*, (Apr. 1976) Abstract.

Sevastianov, O.N., "Using Strontium to Monitor the Flooding of Oil Wells in the Orenburg Field," *Geol Nefti Gaza* (USSR), pp. 32–34 (1980) Abstract no month available.

Sharma, S.K., "Study of Corrosion of Metals in the Marine Environment . . . ", *Hawaii Nat. Energy Insti.*, (1987) Abstract no month available.

Shyong, J., et al., "Analysis of Uranium, Thorium, and Potassium in the Soil and Rocks in the Northwestern Taiwan," *Computer Applications in Health Physics*, pp. 7141–7145 (1984) Abstract no month available.

Simpson, W.R., et al., "In–Situ Deep Water Particle Sampler and Real–Time Sensor Paackage with Data from the Madeira Abyssal Plain," *Inst. Oceanogr. Sci.*, vol. 34, No. 8, pp. 1477–1498 (1987) Abstract no month available.

Singh, U.P., et al., "Sampling the Biscayne Aquifer for Toxic Pollutants," *Conf. on Management of Municipal, Hazardous and Coal Wastes*, Wastes, pp. 422–431 (Sep. 1984) Abstract.

Smith, W.J., et at., "InSitu Gross Alpha Monitoring Technique for Delineating Fugitive Mill Tailings," *Int'l Symp on Management of Waste from Uranium Mining and Milling*, pp. 621–632 (1982) Abstract no month available.

Smyroniotis, C.R., "Mobile Monitoring and Process Simulation for High Heat Flux Cooling Water Systems," *Proc of Instr and Control Systems Conf and Exhibit* pp. 133–444 (1987) Abstract no month available.

Spencer, C.M., "Progress and Performance of On–Line Analyzers of Coal," *Sump on Instr and Control for Fossil Energy Processes*, pp. 619–633 (7 Jun. 1982/Sep. 1982) Abstract.

Stewart, K.K., "Flow Injection Analysis," *Analytical Chem.*, vol. 55, No. 9, pp. 931A, 1040A from No. 11 and attachments (Aug. and Sep. 1983 resp.) Abstract.

Stolzenburg, T.R., et al., "Preliminary Results on Chemical Changes in Groundwater Samples Due to Sampling Devices," *Residuals Management Technology, Inc.*, Madison WI, 110, (Jun. 1985) Abstract.

Stuart, T.P., "Limiting Values for Radionuclide Concentration in the Soil from Remote Spectrometer Measurements," *EG and G, Inc., Las Vegas NV*, 38 (Aug. 1977) Abstract.

Symader, W., et al., "The Dynamics of the Conveyance of Suspended Particles and Its Relevance to Water Quality Problems," *Ann Meeting Fachgruppe Wasserchemie of Gesselschaft Deutscher Chemiker*, pp. 159–169 (Dec. 1991) Abstract.

Takeda, Y., "Development of Ultrasould Velocity Profile Monitor and its Experience," *4th Int'l Topical Meeting on Nuclear Reactor Thermal–Hydraulics*, pp. 418–423 (10–13 Oct. 1989) Abstract.

Takeuchi, M., et al., "Geophysical Monitoring System of Diffusing Electrolyte Injected into Groundwater," *Nat'l Res. Inst. of Agricultural Engineering (Japan)*, pp. 12–18 (25 Mar. 1990) Abstract.

Talmage, S.S., "Comparative Evaluation of Several Small Mammal Species as Monitors of Heavy Metals, Radionuclides and Selected Organic Compounds in the Environment," *Univ of Tenn Thesis*, 193 p (1989) Abstract no month available Tarlov, M.J., et al., "PH Sensors Based on Iridium Oxide," *Eng. Nat'l Inst. of Standards and Tech*, 20 p. (Mar. 1990) Abstract.

Tercier, M.L., "In Situ Voltammetric Measurements in Natural Waters: Future Prospects and Challenges," *Electroanalysis*, vol. 5, pp. 187–200 (1993) no month available.

Toenniben, A., et al., "application of a CW Chemical Laser for Remote Pollution Monitoring and Process Control," *Appl Phys.* vol 18, pp. 297–304 (1979) Abstract no month available.

Vaughan, B.E., "Multitechnology and Supporting Research Programs," *Battelle Pacific Northwest Labs*, pp. 7.1–7.31 (Feb. 1978) Abstract.

Viswambaran, K.R., et al., "Assessment of Background Radiation Levels at Madras Atomic Power Station," *Bullietin Of Radiation Protection (India)*, vol. 11, Nos. 3–4, 161–165 (Jul.–Dec. 1988) Abstract.

Wang, J., *Analytical Electrochemistry*, TEXTBOOK Chapter 2.5, "Controlled Potential Techniques—Stripping Analysis" pp. 27 and 44–53 (1994) no month available.

Wang, J., *Analytical Electrochemistry*, TEXTBOOK Chapter 3.1 "Electrochemical Cells," pp. 69–70 and Chapter 5.1.1 Enzyme–Based Electrodes pp. 134 and 144 (1994) no month available.

Wang, J., "Anodic Stripping Voltammetry as an Analytical Tool," *Environ. Sci. Technol.*, vol. 16, No. 2, pp. 104A–107A (1982) month available.

Wang, J., *Stripping Analysis, Principles, Instrumentation and Applications* TEXTBOOK (1985) no month availabe.

Wang, J., et al., "Anodic Stripping Voltammetry at Ultramicroelectrodes for Metal Speciation Studies in Aqueous Solutions of Low Ionic Strength," *Electroanal. Chem.*, vol. 246 pp. 297–305 (1988) no month available.

Wang, J., "Adsorptive Stripping Voltammetry—A New Electroanalytical Avenue for Trace Analysis," *J. Res of Nat'l Bureau of Standards*, vol. 93. No. 3, pp. 489–491 May–Jun. 1988).

Wang, J., et al., "Batch Injection Analysis," *Analytical Chemistry*, vol. 63, pp. 1053–1065 (1991) no month available.

Wang, J., et al., "Batch Injection Analysis with Termistor Sensing Devices," *Analytical Letters*, vol. 24, No. 8. pp. 1389–1400 (1991) no month available.

Wang, J. et al., "Batch Injection with Potentiometric Detection," *Analytica Chimica Acta.* vol. 252, pp. 215–221 (1991) no month available.

Wang, J., et al., "Mercury–Coated Carbon–Foam Composite Electrodes for Stripping Analysis of Trace Metals," *Analytical Chemistry*, vol. 64, pp. 151–155 (1992) no month available.

Wang, J., et al., "Batch Injection Analysis Using Fiber–Optic Fluorometric Detection," *Applied Spectroscopy*, vol. 46, No. 1, pp. 107–110 (1992) no month available.

Wang, J., et al., "Gold Ultramicroelectrodes for On–Site Monitoring of Trace–Lead," *Electroanalysis*, vol. 5, pp. 809–814 (1993) Abstract Only no month available.

Wang, J. et al., "Organic–Phase Enzyme Electrode for the Determination of Trace Water in Nonaqueous Media." *Analytical Chemistry*, vol. 65 pp. 845–847 (1993) no month available.

Wang, J., et al., "Amperometric Biosensor for Phenols Based on a Tyrosinase–Graphite–Epoxy Biocomposite," *Analyst*, vol. 119, Abstract (Mar. 1994).

Wang, J., et al., "Stripping Potentiometric Measurements of Copper in Blood Using Gold Microelectrodes," *Analytica Chimica Acta*. vol. 286, pp. 189–195 (1994) no month available.

Wangsa, J., et al., "Fiber–Optic Biosensors Based on the Fluorometric Detection of Reduced Nicotinamide Adenine Dinucleotide," *Anal. Chem.* vol. 60, pp. 1080–1092 (1988) no month available.

Wertenbach, H., "Determination Methods for Plutonium as Applied in the Field of Reprocessing," *Seminar on Determination Methods for Plutonium as Applied in the Field of Reprocessing*, pp. 77–96 (15 Oct. 1992/Jul. 1983) Abstract.

Wang, J., "Decentralized Electrochemical Monitoring of Trade Metals: From Disposable Strips to Remote Electrodes," *Analyst*, vol. 119 pp. 763–766 (May 1994).

Winkelmann, L., et al., "Radionuclide Deposition and Exposure in the Fed Rep of Germany after the Chernobyl Accident," *Oak Ridge National Lab. TN (USA)*, 30 p (Nov. 1989) Abstract.

Wogman, N.A., "In–Situ X–Ray Fluorescence and Californium–252 Neutron Activation Analysis for Marine and Terrestrial Mineral Exploration," *IAES Int'l Symp on Nuclear Techniques in Exploration, Extraction and Processing of Mineral Resources*, pp. 447–461 (1977) Abstract no month available.

Wogman, N.A., "Development and Application for an In Situ X–Ray Fluorescence Spectrometer for Underwater Sediment Analysis," *Environ, Int.*, vol. 4, No. 4, pp. 313–324 (1980) Abstract no month available.

Wring, S.A., et al., "Chemically Modified, Screen–Printed Carbon Electrodes," *Analyst*, vol. 117 pp. 12811282 (1992) no month available.

Yoneda, K.T., "Characteristics and Correlation of Various Radiation Measuring Methods in Spatial Radiation Measurement," *Ann Report of Niigata Prefectural Res. Lab for Health and Environ.*, pp. 156–162 (Oct. 1992) Abstract.

Zauke, G.P., et al., "Biological Indicators of Environmental Quality in the Elbe, Weser and Ems Estuary," *Biologie Umweltbundesamt, Berlin (Germany, F.R.)*, 156 p (Jul. 1986) Abstract.

Zirino, A., et al., "Measurement of Cu and Zn in San Diego Bay by Automated Anodic Stripping Voltammetry," *American Chem Soc*, vol. 12, No. 1, Abstract (Jan. 1978).

REMOTE ELECTROCHEMICAL SENSOR

GOVERNMENT RIGHTS

The Government may have rights to this invention pursuant to Contract No. DE-FC04-90AL63805 awarded by the U.S. Department of Energy Waste Management Education and Research Consortium (WERC).

BACKGROUND OF THE INVENTION

1. Field of the Invention—Metals

The present invention relates to remote, on-site, continuous monitoring of metals and organic compounds, particularly phenolic compounds.

2. Background of Invention—General

Detection and monitoring of metals and organic compounds is normally done by having an operator collect on-site field samples and then taking the samples back to a laboratory.

Attempts have been made to provide both remote field sampling and analysis, on-site. See U.S. Pat. No. 5,120,421, entitled Electrochemical Sensor/Detector System and Method to Glass et al., and U.S. Pat. No. 5,296,125, entitled Electrochemical Sensor Detector System and Method to Glass et al. However, an operator is still required to be present on-site to collect the sample, and the device does not communicate directly with the laboratory.

3. Background of Invention—Metals

Contamination of hazardous waste sites and groundwater with toxic heavy metals (e.g. Hg, Pb, U, As, Cr, Al) represents a major national problem. Site monitoring and surveillance programs are required for a closer control of metal pollutants. The traditional use of atomic-spectroscopy central-laboratory measurements of heavy metals is too expensive and time consuming. Also, samples often change composition during their collection, transport and delay before analysis, ultimately producing unreliable results. Innovative field deployable methods are highly desired for the task of site characterization and remediation, as they minimize the huge labor analytical costs, and provide timely data for real-time emergencies and decision making. Chemical sensors are particularly attractive for providing real-time, remote monitoring of priority pollutants. While fiber-optic probes have been suggested for monitoring organic contaminants, no chemical sensor technology has demonstrated capability for remote monitoring of trace metals. (See W. Chudyk, et al., J. Anal. Chem. 1985, 57, 1237.) Clearly, a cost effective metal-sensor technology, capable of monitoring the metal both in time and location, is needed to support the characterization and remediation of hazardous waste sites. (See G. Batiaans, et al., (Eds.), "Chemical Sensors: Technology Development Planning," U.S. Department of Commerce, Springfield, 1993.)

In the present invention, there is provided a remote sensor for in-situ monitoring of trace metals. The compact instrumentation and low power needs of electrochemical techniques satisfy many of the requirements for on-site metal analysis. Particularly attractive for in-situ monitoring of metal contaminants is the remarkably sensitive technique of stripping analysis. (See J. Wang, "Stripping Analysis: Principles, Instrumentation, and Applications," VCH Publishers; Deerfield Beach, Fla., 1985.) The extremely low (subnanomolar) detection limits of stripping analysis are attributed to its "built-in" preconcentration step, during which the target metals are deposited onto the working electrode.

The feasibility of using stripping analysis for field-based operations was demonstrated first by the U.S. Navy, who developed an automated flow system, based on a mercury-coated open tubular electrode, for continuous shipboard monitoring of trace metals in oceans. (See A. Zirino, et al.; C. Environ. Sci. Technol., 1978, 12, 73.) Another useful flow system (based on a hanging mercury electrode) was deployed by Buffle's group for in-situ metal monitoring in lakes and oceans. (See M. Terrcier, et al., J. Electroanalysis, 1993, 5, 187.) Yet, submersible (downhole) sensors based on stripping analysis have not heretofore been developed due to several technical difficulties (e.g., use of mercury surfaces, needs for oxygen removal, and solution stirring or supporting electrolyte) which prevent continuous remote operations.

The field probe of the present invention addresses these challenges by combining several stripping methodologies. In the preferred embodiment, these include the replacement of the traditional mercury electrodes with gold surfaces (see J. Wang, et al., Electroanalysis, 1993, 5, 809; J. Wang, Anal. Chim. Acta, 1994, 286, 198; E. P. Gil, et al., Anal. Chim. Acta, 1994, 293, 55), the use of ultramicroelectrodes which offers efficient mass transport (independent of natural convection) as well as work in low ionic-strength natural waters (see J. Wang, et al., J. Electroanal. Chem., 1989, 246, 297; J. Huiliang, et al., Anal. Chem. Acta. 1987, 193, 61) and the incorporation of potentiometric stripping analysis (PSA) which eliminates the need for oxygen removal and minimizes the surfactant effects (see D. Jagner, Trends Anal. Chim. Acta, 1993, 273, 35; P. Ostapczuk, Anal. Chem. Acta, 1993, 273, 35). Such combination of gold ultramicroelectrodes with PSA thus facilitates remote operations by making solution stirring or deoxygenation, electrolyte addition or mercury electrodes unnecessary. These electrochemical considerations are coupled with the need for a compact and rugged probe, hence ensuring that the in-situ sensor performs comparable to established laboratory-based stripping instruments.

4. Background of Invention—Phenolic Compounds

Because of the inherent toxicity of phenolic and other organic compounds, there is a considerable interest in their determination in environmental matrices. Such assays in environmental samples are usually carried out in central laboratories using separation techniques such as liquid chromatography. However, in view of the huge labor and analytical costs or time delays associated with centralized laboratory analyses, there are immediate needs for developing field sensors for organic compounds. A real-time continuous monitoring capability, in particular, should give rapid warning in case of sudden contamination, provide rapid feedback during site remediation activities, and be valuable for studying processes in an aquifer. Field sensors for organic compounds thus greatly improves the quality and efficiency of site monitoring or remediation activities.

Tyrosinase-based enzyme electrodes have been shown useful for the selective determination of phenols in environmental matrices (see M. Bonakdar, J. Electroanal. Chem. 1989, 266, 47; J. Wang, et al., Analyst, 1994, 419, 455; L. Campanella, et al., Analyst, 1993, 118, 979; F. Ortega, et al., J. Pharm. Biomed. Anal., 1992, 10, 789). Such devices commonly rely on the reductive amperometric detection of the liberated quinone species. For this purpose, tyrosinase is immobilized onto the transducer surface or incorporated (mixed) within a carbon paste matrix. However, enzyme-based remote electrodes, capable of making continuous real-time measurements at large sample/instrument distances, have not been reported.

SUMMARY OF THE INVENTION
(DISCLOSURE OF THE INVENTION)

The present invention relates to electrochemical sensing. The preferred sensor and method of the invention comprises an electrode assembly for contacting at least one constituent in a remote location, a long (10 or fewer to more than 100 feet) communications cable for connecting the electrode assembly from the remote location to an analysis location, and an analysis device for analyzing constituent information obtained from the electrode and communicated to the analysis device via the long communications cable.

The preferred electrode assembly comprises a three-electrode assembly; a working electrode, a reference electrode and a counter electrode. The electrode is electrochemically reactive with the constituent. The electrode preferably comprises a metal (e.g. gold or silver) or carbon when the constituent comprises a metal. The electrode preferably comprises an enzyme (e.g. tyrosinase) when the constituent comprises an organic compound (e.g. a phenolic compound). The electrode may comprise a fiber or arrays or other structures.

The sensor preferably comprising preconcentration and stripping functions and additionally a cleaning function. All of these functions are preferably accomplished in less than 5 minutes. The sensor performs continuous, timed monitoring and analysis (e.g. 15 runs/analyses per minute).

A primary object of the present invention is to provide remote and continuous monitoring and sensing of metals and organic compounds.

A primary advantage of the present invention is that remote on-site accurate monitoring can be made without requiring continuous on-site field personnel.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention provides for remote sensing. The remote sensors can detect metals or organic compounds in-situ in a wide range of natural waters and aqueous industrial process streams.

The present invention further provides for a portable, battery or electrically operated, fully automated microprocessor-controlled instrument, capable of unattended operation (in the stripping or amperometric modes), "smart" data processing and signal transmission to a laboratory or analysis center.

METAL SENSOR

The probe design of the invention for remote sensing of metals aims at addressing both electrochemical and environmental requirements, namely the achievement of an optimized stripping performance, as well as compatibility with remote field work (e.g., downhole or shipboard or other water monitoring). The electrochemical considerations are thus coupled with the need for a rugged device and rapid maintenance (e.g., fast replacement of electrodes).

Figure 1:
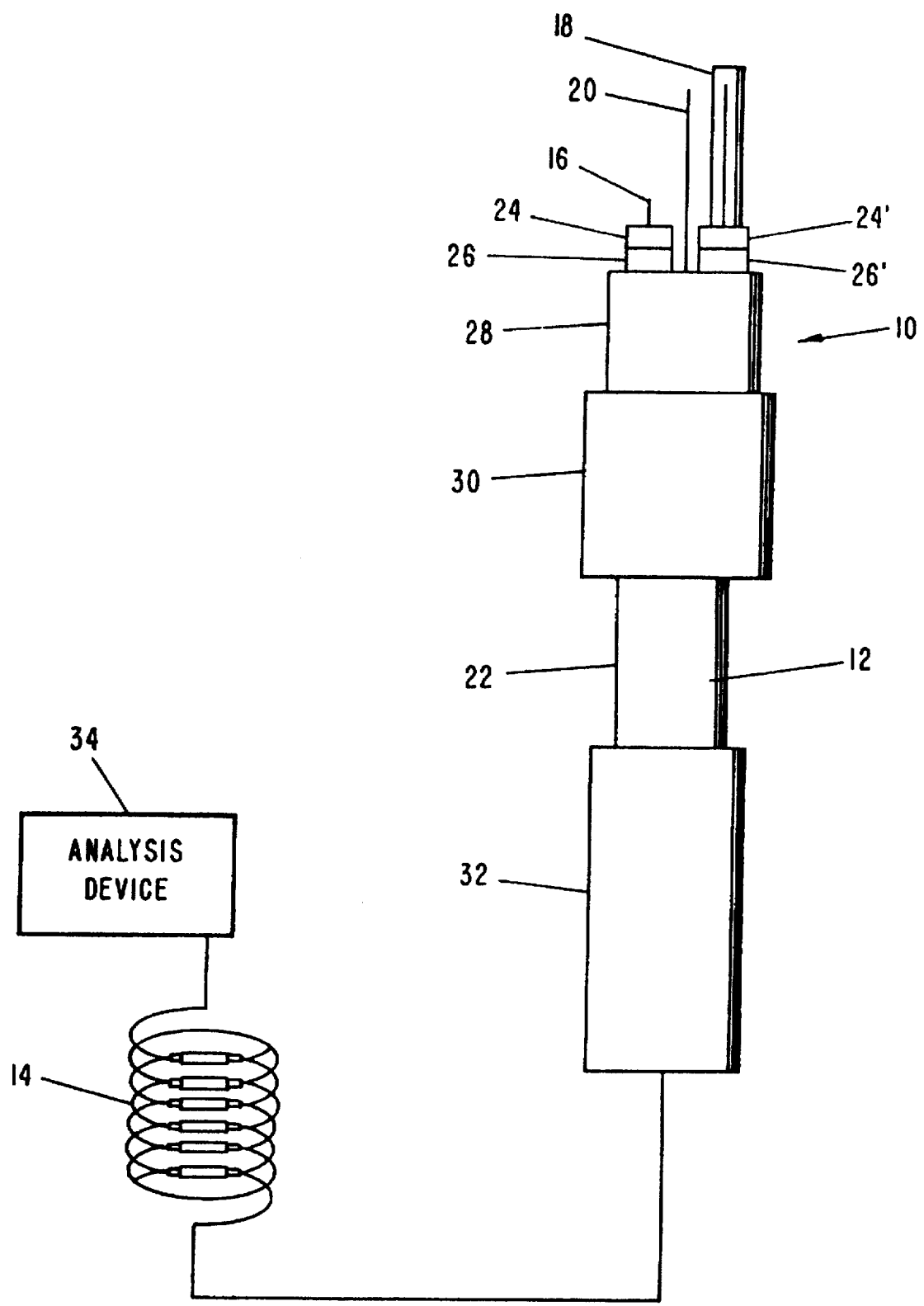
FIG. 1 is a front and schematic view of the preferred metal sensor of the present invention.

The preferred sensor, shown in FIG. 1, comprises an electrode assembly 10 connected (through environmentally-sealed connectors 12) to a long, shielded communications cable 14 (e.g. 10 feet to more than 100 feet). The shielded cable 14 assures a negligible electrical noise even for large instrument/sample distances (e.g. hundreds of feet). The microelectrode 16, where the deposition/stripping reactions of interest take place, represents the heart of the probe. This microelectrode 16 is preferably made of gold fiber, but other metals, carbon and structures/configurations (e.g., screen printed or lithographically-made strip, wire, band, arrays, deposit or film on a substrate, etc.) can be utilized in the invention. The transducer surface of the microelectrode 16 is chosen based on the metal to be detected. Gold surfaces offer convenient quantitation of environmentally-relevant trace metals (such as copper, lead, selenium, arsenic, or mercury). Although one advantage of the present invention is to replace mercury-based electrodes, mercury systems can be utilized in accordance with the invention, depending on the metal being detected. Measurements of lead and copper with a gold microelectrode compare favorably with those observed at mercury-based sensors. The microelectrode configuration obviates the need for solution stirring during the deposition step, and allows measurements with little (or no) supporting electrolyte. Its coupling to a PSA operation also eliminates the need for a time-consuming deoxygenation step. Such simplified operation thus meets many of the requirements for remote chemical sensing.

The electrode assembly sensor tip comprises three electrodes, the working microelectrode 16 (again, preferably gold fiber), a reference electrode 18 and a counter electrode 20. These three electrodes 16, 18, 20, are connected to the long shielded cable 14 via an environmentally-sealed connector 22 (e.g. silicone or rubber). Electrode sensing information is then communicated via the long shielded cable 14 to an analysis device 34 (e.g. a voltammograph).

In the preferred embodiment, the working electrode 16 and reference electrode 18 are sealed into fittings 24, 24', disposed in coupling connectors 26, 26' which are further disposed in housings 28, 30. This arrangement provides for easy removal of these electrodes 16, 18. An additional housing 32, provides further stability.

Real time, continuous monitoring is possible using the probe of the present invention. The analytical utility of the remote probe is based on the linear correlation between PSA response and the target metal or contaminant concentration. Only several minutes (e.g. 3–5) are required for the entire deposition/stripping/cleaning cycle. Numerous tests can therefore be made (e.g. 15–20 runs per hour).

The invention is further illustrated by the following non-limiting examples.

EXAMPLE I

Experimental Results—Metals

A three-electrode assembly (100-μm diameter, 5-mm long gold microcylinder working electrode, silver-silver chloride reference electrode (BAS Model RE-4) and a platinum wire counter electrode contained in a PVC housing, was connected to a long shielded cable, via a 3-pin environmentally-sealed rubber connector. The gold microelectrode was fabricated as described in e.g. J. Wang, et al., *Anal. Chim. Acta*, 1994, 286, 189. Both the working and reference electrodes were sealed into Teflon® fittings, screwed into female coupling connectors, which were fixed with epoxy in the PVC housing. The counter electrode was fixed permanently into the housing with epoxy. Electrical contact to the working and reference electrodes was accomplished with the aid of brass screws and spring assemblies, contained inside 7-mm o.d. copper tubes. The latter were placed within the female connectors, and were soldered to the copper wire contact. The other end of the copper wires was connected to the male environmentally-sealed connector. Another copper wire was used to connect the platinum electrode to the environmentally-sealed connector. The entire assembly was sealed into the PVC housing. The 3-pin male connector (Newark Electronics) was connected to the receptable, which was attached to the shielded cable. Such connection permits quick disconnection of the electrode housing from the cable. The female connector was sealed in a PVC tube that provides additional stability. A 3-cm diameter PVC tube was threaded onto the housing unit to protect the electrode assembly during field testings. Cables of different lengths, ranging from 25 to 100 ft., were employed in accordance to the specific field application.

Apparatus

Potentiometric stripping experiments were performed using a TraceLab potentiometric stripping unit (PSU 20, Radiometer, Copenhagen), in connection with an IBM PS/55SX or Thinkpad Laptop computers. The manual instrument used in the examples was compact, 10×6×3 inches, and light weight (8 lb). Some experiments were carried out with a smaller microprocessor-controlled "homemade" PSA analyzer.

Reagents

All solutions were prepared with double-distilled water. Stock metal solutions were prepared daily from the corresponding 1000 ppm atomic absorption standards (Aldrich). Experiments were carried out in unpreserved groundwater (from Hanford Site, Richland, Wash.) or seawater (San Diego Bay, Calif.) solutions without additional supporting electrolyte.

Procedure

Laboratory experiments and field pre- or post-calibrations were performed in a 400 mL Erlenmeyer flask into which the entire probe was immersed. A silicone-grease was applied to all connectors (to ensure sealing needed for preventing entry of solution). Prior to the deposition step, the gold electrode underwent a "cleaning" procedure for 1–2 min at +0.5 to +1.0V (depending on the target metals). Deposition proceeded in the quiescent solution for 1–2 min at potentials ranging from −0.3 to −0.7V (depending upon the sought-for metal(s)). After the deposition period, the potentiogram was recorded by applying a constant oxidation current (in the 0.3–2.0 μA range) and the BASE 3 or 4 commands of the Trace Lab software for baseline treatment. A similar PSA protocol was employed when measurements were made in the field (for in-situ monitoring of seawater or groundwater).

Figure 2A:
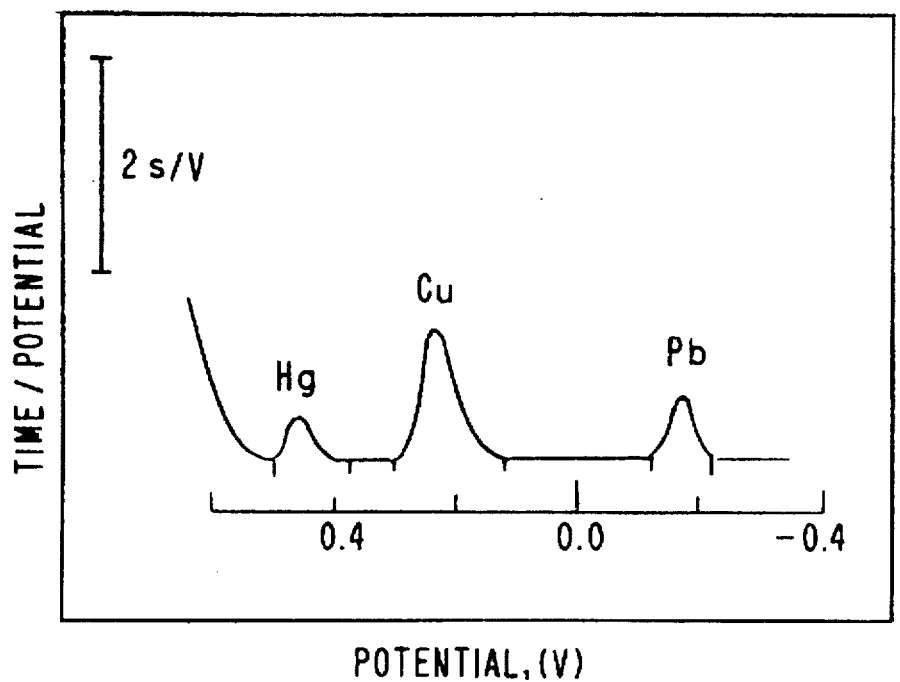
FIG. 2 shows graphs of the stripping potentiometric response of the sensor of FIG. 1 to untreated seawater (A) and groundwater (B) containing metal contaminants.
Figure 2B:
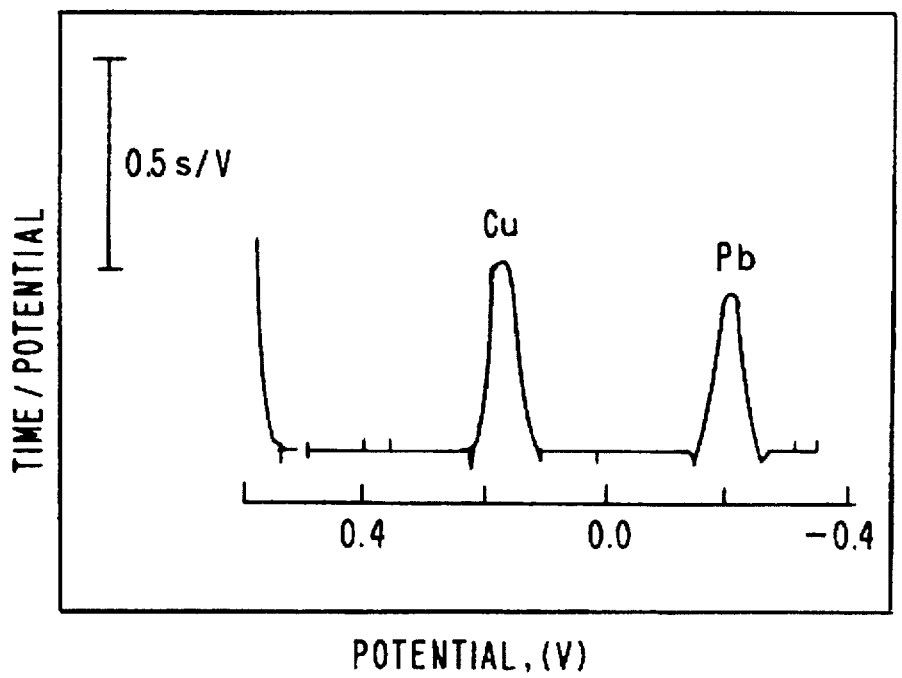

FIG. 2 displays the stripping potentiometric response of the sensor to unpreserved seawater (A) and groundwater (B) samples, spiked with 5–10 μg/L (ppb) levels of lead, copper and mercury. Well-defined and sharp peaks are observed, despite the use of nondeaerated samples, unstirred solutions or short (1–2 min) deposition periods. The well-resolved peaks (ΔEp>0.2V) and the flat baseline allow convenient multielement determinations of low μg/L concentrations in these unpreserved samples. The exact peak potentials (around −0.2V (Pb), +0.2V (Cu) and +0.45V (Hg)) depend on the extent of binding to complexing agents present in these samples. The copper peak (in the seawater medium) increased linearly with the preconcentration time (up to 10 min), while the lead peak increased sigmoidally upon changing the deposition potential between −0.3V and −1.0V (with a plateau reaching above −0.5V (not shown)). Overall, a deposition potential of −0.5V allowed simultaneous measurements of all three metals, while a lower one (−0.3V) was preferred for the copper-mercury pair. (More positive deposition potentials extend the anodic potential window, as desired, for measurements of metals with relatively positive stripping potentials.) Analogous stripping voltammetric measurements (using the rapid square-wave mode) yielded an inferior performance (with convenient quantitation only above the 10 μg/L level) due to a higher baseline response (not shown). The computerized PSA instrument is superior in addressing background contributions associated with the gold surface. Yet stripping voltammetry may also be feasible for operation at the μg/L concentration range.

Figure 3A:
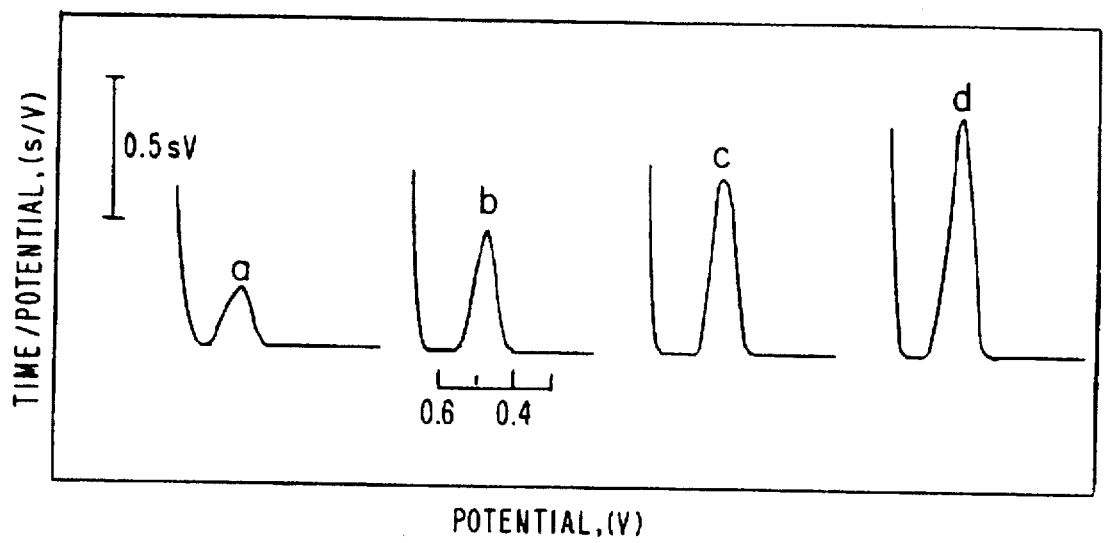
FIG. 3 shows graphs of the stripping potentiometric response of the sensor of FIG. 1 to groundwater solutions containing increasing levels of (A) mercury and (B) selenium.
Figure 3B:
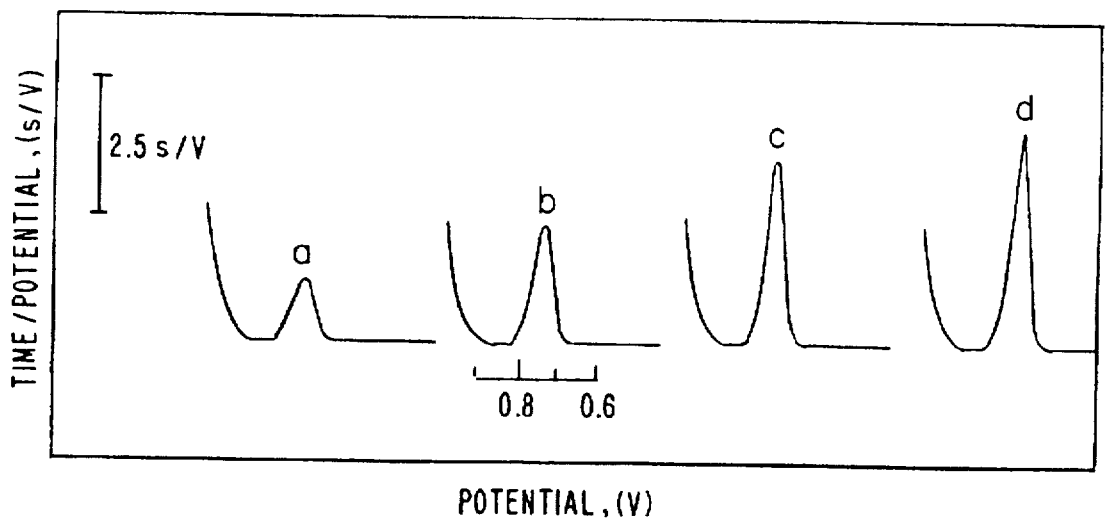

FIG. 3 displays stripping potentiograms, following one-min deposition, for unstirred groundwater solutions containing increasing levels of (A) mercury and (B) selenium (in 20 μg/L steps). These peaks are part of a series of ten concentration increments over the 10–100 μg/L range. The well-defined peaks increase linearly with the metal concentration over the entire range. Linearity up to 100 μg/L was observed also in analogous calibration experiments for lead and copper (not shown). The dynamic range of the probe can be changed by adjusting the deposition time. Detection limits of 0.7 µg/L copper and 1.1 µg/L lead were estimated from the response, following one-min deposition, for a groundwater sample containing 5 and 10 µg/L of these metals (e.g., see FIG. 2B). Even lower detection limits can be achieved by further extending the deposition time. Overall, ca. 3–4 min are required for the entire deposition/stripping/cleaning cycle (for quantitation at the 1–20 µg/L range), thus leading to near real-time monitoring at a rate of 15–20 runs/hour.

Figure 4A:
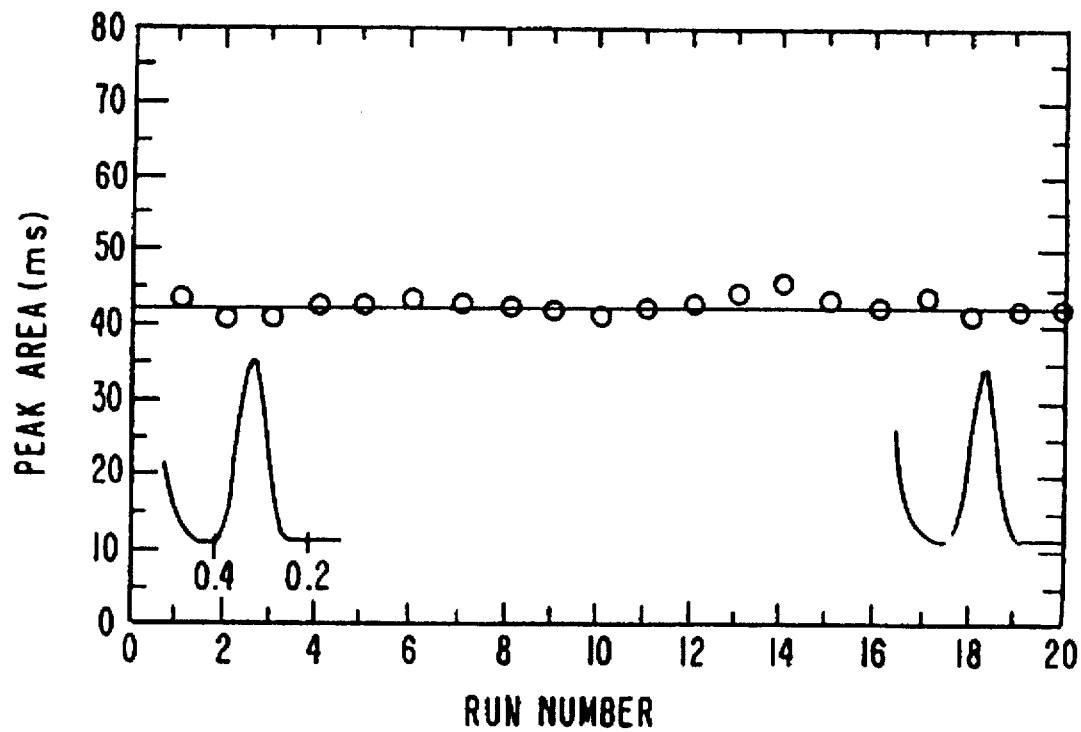
FIG. 4 shows graphs of the stability of the stripping potentiometric response of the sensor of FIG. 1 to groundwater solutions during a long run of 20 successive measurements of copper (A) and lead (B)
Figure 4B:
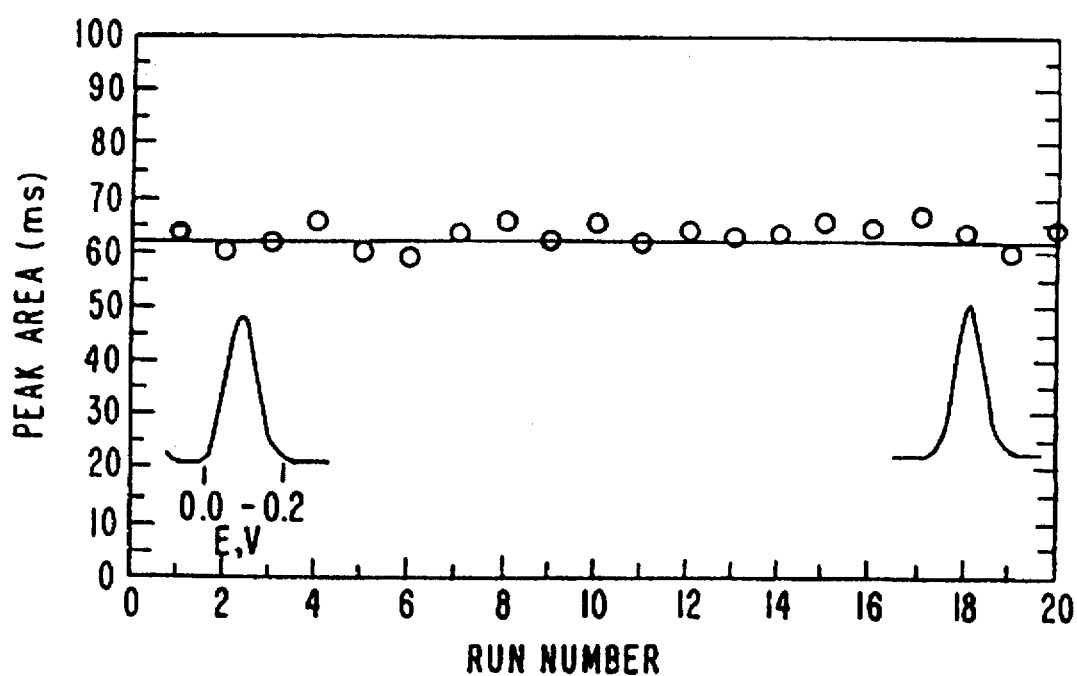

High measurement stability is an important requirement for the remote in-situ probe. The short "cleaning" step insures complete removal of the deposited metal at the end of each run, and hence a "fresh" (analyte-free) gold surface prior to the next measurement. Hence, the deposition/ stripping cycle leads to a reversible sensor behavior. FIG. 4 examines the stability of the response during a long run of 20 successive measurements of copper (A) and lead (B) in groundwater. A highly stable response is observed over these prolonged (50–70 min) operations. The relative standard deviations for these complete series were 2.1% (A) and 3.2% (B). High stability was also observed in longer (3–5 hours) field testings, described below. The stable response in unpreserved natural water samples is also attributed to a minimal surfactant effect associated with the use of PSA and gold surfaces. Whenever needed, the probe construction permits a fast and easy replacement of electrodes. A proper sealing of all connectors (e.g. by coverage with silicone grease) is essential to achieve such stable response, through prevention of liquid entry into electrical contacts.

Figure 5A:
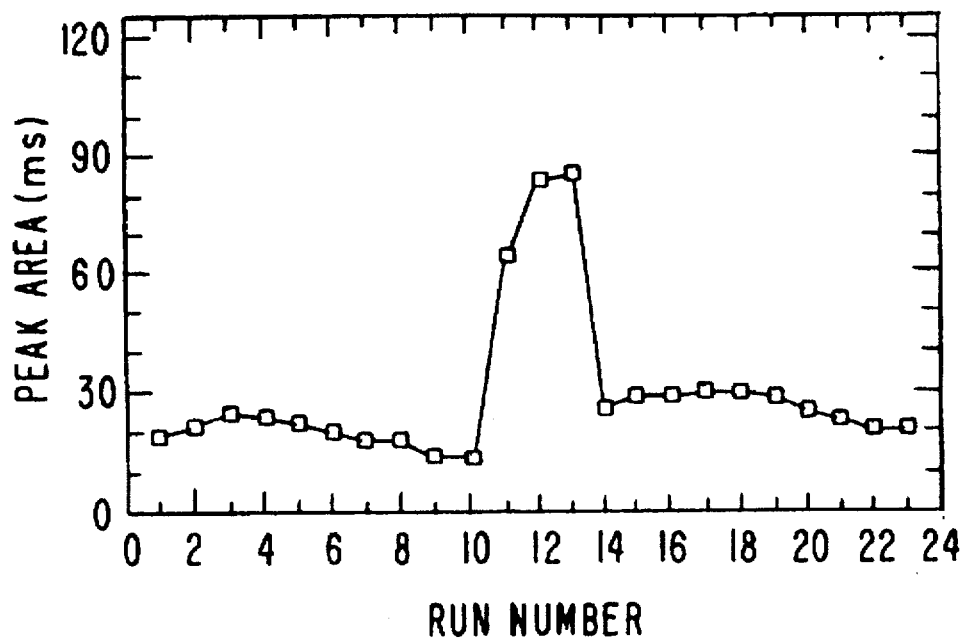
FIG. 5 shows graphs of the ability of the sensor of FIG. 1 to follow sudden changes in concentrations of copper (A) and lead (B)
Figure 5B:
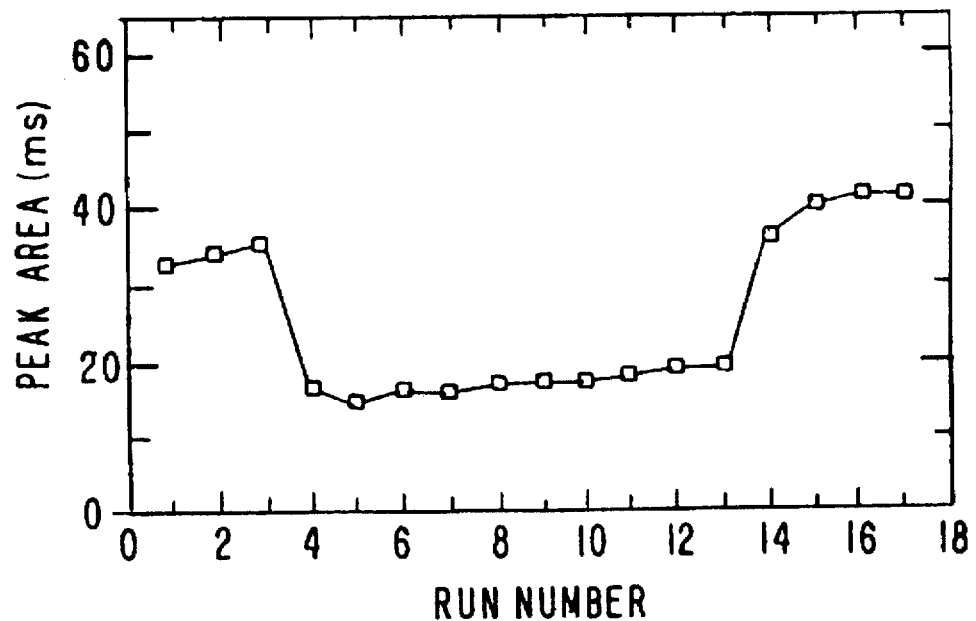

The ability of the remote probe to follow sudden changes in the concentration of copper and lead is illustrated in FIG. 5. The temporal profile, shown in (A), resembles a sharp contaminant release, with 10 runs in a 10 µg/L copper solutions, followed by three replicates in a 40 µg/L solution, and 10 measurements at the original 10 µg/L level. The response rises rapidly from the 10 µg/L baseline upon immersing in the 40 /µg/L solution, and decays sharply upon returning to the original low-concentration medium. Similarly, minimum carry-over effects are indicated from (B), involving three replicates at the 20 µg/L lead level, 10 runs in a 10 µg/L solution, and return to the original 20 µg/L one. These data show how precalibration and/or postcalibration techniques can be utilized with the same protocol employed during the in-situ runs.

Several on-site demonstrations were successfully performed, including a downhole groundwater monitoring and an in-situ shipboard seawater analysis. FIG. 6 shows a stripping potentiogram for groundwater (A) and seawater (B).

The groundwater well (A) was at the Hanford Site (Richland, Wash.). Such in-situ PSA response was obtained at a depth of 40 ft., and is a part of a continuous 3h downhole operation at different depth intervals (35–55 ft). A small copper peak (at ca. +0.25V) was observed in these repetitive runs. Such response corresponds to 3 µg/L, as was confirmed in subsequent ICP/MS measurements. No apparent electrical noise was observed despite the significant cable length.

Figure 6B:
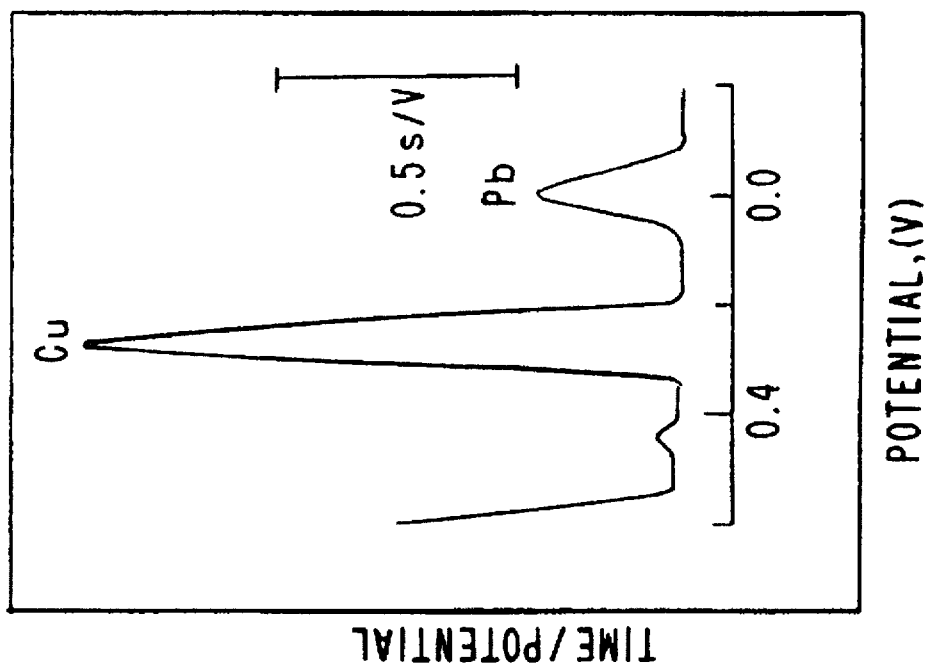
FIG. 6 shows graphs of the response of the sensor of FIG. 1 in groundwater (A) and seawater (B)
Figure 6A:
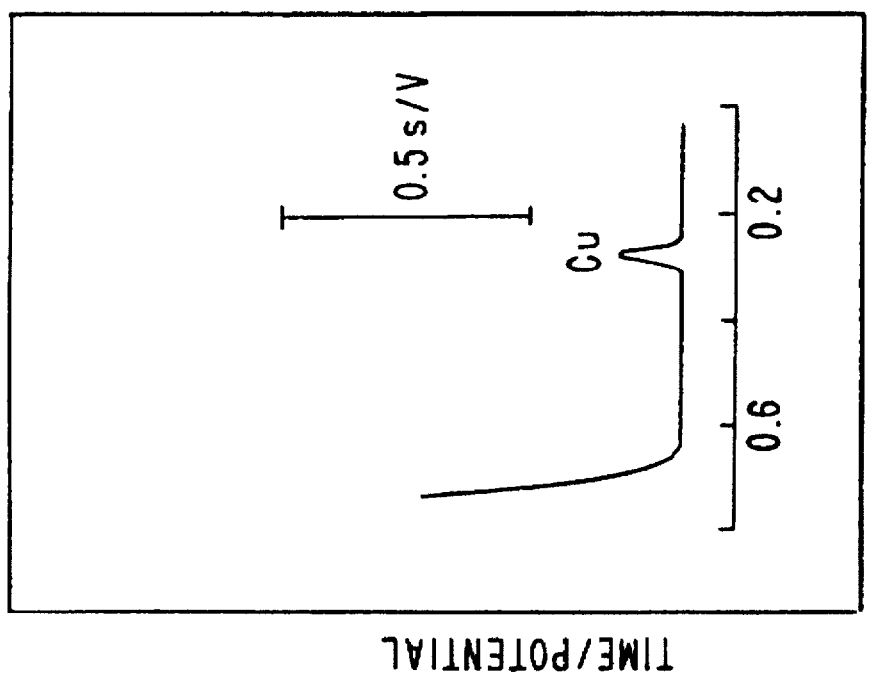

FIG. 6(B) illustrates the response of the in-situ probe for seawater in San Diego Bay (California). Such measurement was made from a small boat, with the probe dangling from the side of the vessel just below the water surface. It was part of a 5-hour in-situ study at different locations in San Diego Bay. On-boat precalibration experiments, employing a spiked seawater sample, were used for computing the concentration. Large copper and lead peaks, corresponding to 11 and 2 µg/L, respectively, were observed. Such relatively high levels were anticipated for this specific location (the south embayment, "pocket," of Shelter Island), where discharge from pleasure boats and restricted circulation exist. Substantially lower copper and lead levels (of 0.9 and 0.7 µg/L, respectively) were detected at the mouth of the bay (around Point Loma), as expected for the metal distribution in San Diego Bay (see A. Zirino, et al.; *C. Environ. Sci. Technol.*, 1978, 12, 73). Such values indicate that contamination from the boat did not contribute to the sensor response.

The above examples illustrate the utility of stripping-based electrochemical sensors for remote monitoring of trace metals. The remote probe offers significant advantages for in-situ measurements of priority metal contaminants, including remarkable sensitivity, multielement and speciation capabilities, high selectivity, small size and low cost. Such coupling of metal ultramicroelectrodes with PSA overcomes difficulties associated with the adaptation of traditional stripping procedures to long-term remote operations. Additional stripping procedures (e.g. absorptive stripping) or ligand-modified electrodes can be incorporated for monitoring additional analytes. The probe can be further miniaturized to permit adaptation to cone penetrometer technology.

ORGANIC COMPOUND SENSOR

Figure 7:
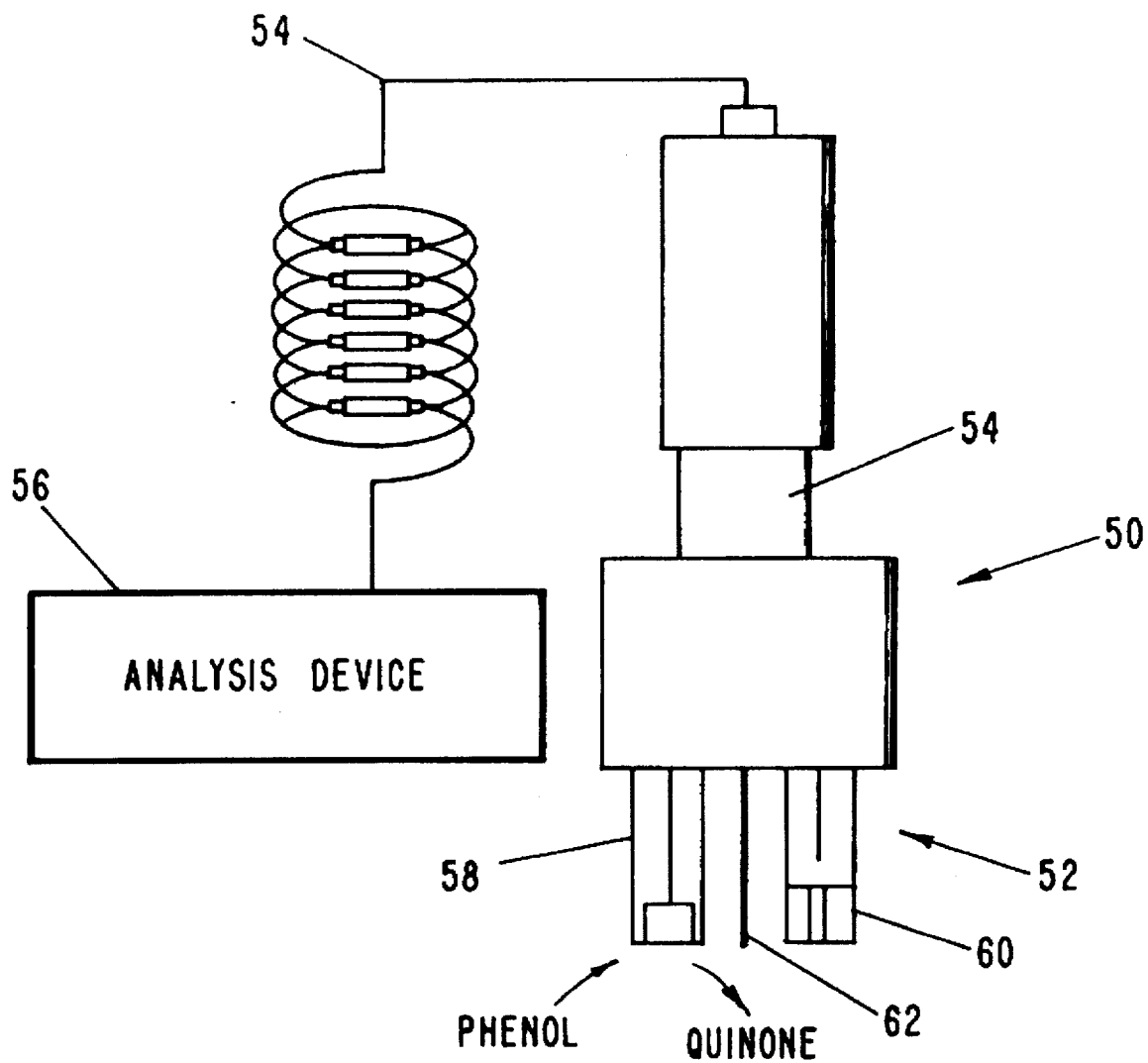
FIG. 7 is a front and schematic view of the preferred biosensor of the present invention.

In another embodiment of the invention, for detecting organic compounds, the preferred sensor addresses key environmental and electrochemical requirements, namely the achievements of an optimized biosensing performance and compatibility with remote field work. The preferred remote enzyme sensor 50 is shown in FIG. 7. The sensor 50 includes a specially designed bioelectrode assembly 52 (comprising an enzyme electrode 58 a reference electrode 60 and a counter electrode 62), connected (via environmentally sealed connectors 54 (similar as shown in FIG. 1)) to a long (e.g., 10 feet to more than 100 feet) shielded communication cable 54 and then to an analysis device 56 (e.g. a voltammograph).

The preferred probe 50 comprises a specially designed (preferably tyrosinase) enzyme electrode (e.g. tyrosinase for phenol measurements) coupled to the shielded cable 54. The combination of biocatalytic recognition and amperometric transduction offers highly selective measurements of micromolar concentrations of organic compounds in unpreserved river and groundwater samples. Remote monitoring of the compounds is provided via a judicious selection of the biorecognition element. Such elements include an enzyme, antibody, whole cell or receptor.

The biosensing considerations are thus coupled with the need for rugged and compact devices, large instrument-sample distances and rapid maintenance. In addition, operational conditions are optimized to meet the specific requirements of remote operation.

While the examples illustrate a remote enzyme electrode presented within the framework of phenol sensing, it can be utilized to detect other relevant pollutants through a proper choice of the biocatalyst. Similar enzyme-based probes can be utilized for other pollutants (e.g., sulfite, peroxide, formaldehyde) via a choice of the biocomponent. Different enzyme tips may be mounted on the same probe to allow simultaneous detection of several contaminants.

There are several technical challenges associated with the adaptation of tyrosinase electrodes, and electrochemical biosensors in general, to remote environmental sensing. Unlike laboratory-based biosensing applications, where the solution conditions can be adjusted for optimal performance, remote operations rely on the use of the natural conditions (e.g., pH, ionic strength, convection). In addition, the in-situ continuous probe of the present invention offers a stable and fast response, with no apparent carry over.

EXAMPLE II

Experimental Results—Phenolic Compounds

The probe consisted of a three-electrode assembly (in a 25-mm i.d. PVC housing tube), connected to a 50-ft long shielded cable, via a 3-pin environmentally sealed rubber connector (Newark Electronics). Two female coupling connectors, fixed with epoxy in the PVC tube, served for mounting the enzyme electrode and silver-silver chloride reference electrode (Model RE-4, BAS). These electrodes were sealed into Teflon male fittings, hence allowing their easy and fast replacement. A platinum wire counter electrode was fixed permanently into the housing. Contact to the enzyme and reference electrodes was made via brass screws and spring assemblies, contained inside 7-mm o.d. copper tubes. The latter were placed within the female connectors, and were soldered to copper wire contacts. The other end of these wires was connected to the male environmentally sealed connector. A similar contact was made to the platinum counter electrode. The male connector was coupled to the receptacle, which was attached to the shielded cable. Such arrangement allowed for rapid disconnection of the electrode housing from the cable. The female connector was also sealed in a PVC tube that provided additional rigidity.

Apparatus and Procedure

Experiments were performed with a Bioanalytical systems (BAS) Model CV-27 voltammetric analyzer, in connection with a BAS X-Y-t recorder. The manual instrument used in the examples was compact, 10×6×3 inches, and light weight (8 lb). The electrode housing was immersed in the sample solution, contained in a 300 ml beaker, and located 50 feet from the voltammetric analyzer. Chronoamperometric experiments were conducted by applying a potential step (to O.OV) and recording the resulting current transient. Quantitative information was obtained by sampling the current after 60 second. All experiments were carried out at room temperature.

Carbon Paste Preparation

The enzyme-containing paste was prepared by hand mixing first 10 mg (42,000 units) of tyrosinase with 4 mg of a polyethylenimine (PEI) stabilizer. This mixture was added to 186 mg of unmodified carbon paste (65% w/w Acheson 38 graphite powder/35% w/w Aldrich mineral oil). Mixing proceeded for 30 minutes. A portion of the resulting paste was then packed firmly into the cavity of the working electrode body (BAS, Model MF-2015). The paste surface was smoothed on a weighing paper.

Reagents

All solutions were prepared with deionized water. Tyrosinase (from mushroom, EC 1.14.18.1, 4,200 units/mg) was utilized from Sigma (catalog number 5-7755). Phenol was received from J. T. Baker, while p-cresol was purchased from Aldrich. Tests were carried out using a phosphate buffer solution (pH 5.5, 5 mM) and unpreserved Hanford-Site groundwater and Rio Grande river water (collected at Richland, Washington and Las Cruces, N. Mex., respectively).

Procedure

The tyrosinase carbon paste electrode is where the biocatalytic recognition took place. The immobilized tyrosinase catalyzed the o-hydroxylation of phenolic compounds to catechols, with subsequent dehydrogenation to o-quinones. Low potential detection of the quinone product thus allowed convenient measurement of environmentally-relevant phenolic substrates down to the submicromolar level.

Figure 8A:
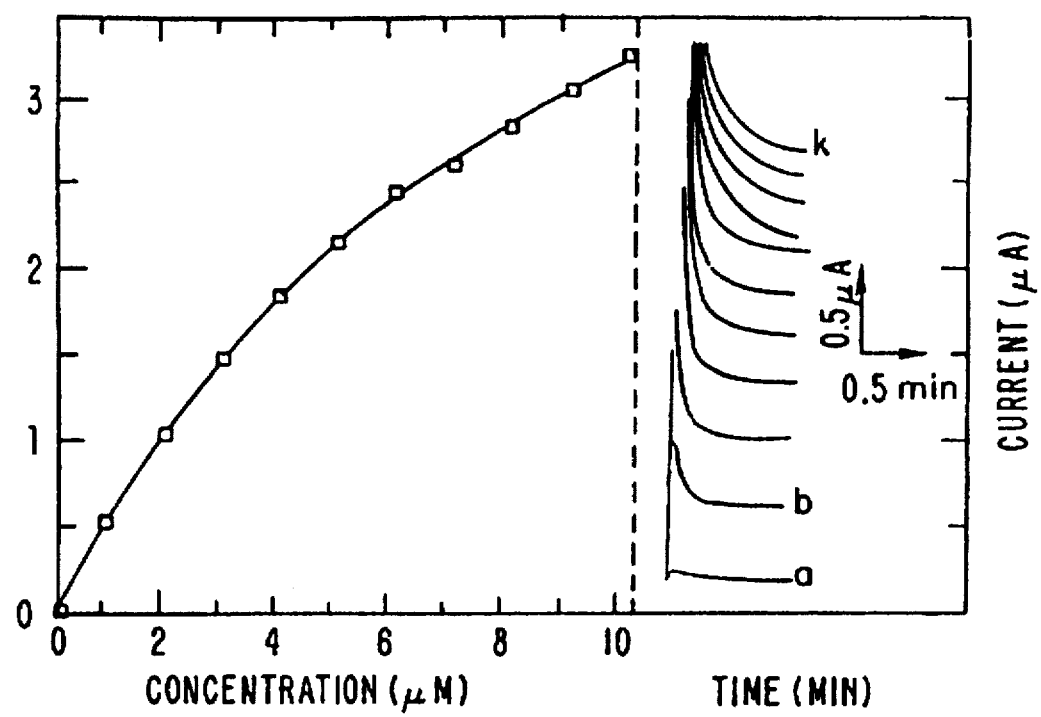
FIG. 8 shows graphs of the chromoamperometric response of the sensor of FIG. 7 to cresol (A) and phenol (B)
Figure 8B:
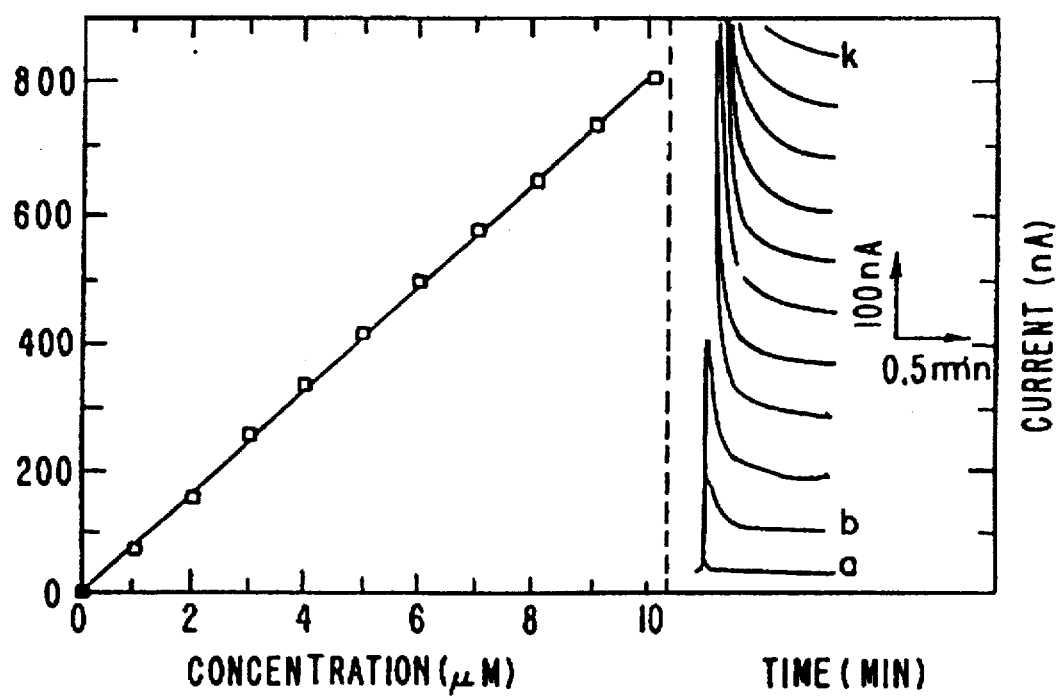

FIG. 8 displays the chromoamperometric response of the remote sensor to cresol (A) and phenol (B) solutions of increasing concentration (in $1\times10^{-6}$ steps, b–k). The probe responded favorably to these micromolar concentration changes. Detection limits around $2\times10^{-7}$M cresol and $3\times10^{-7}$M phenol were estimated based on the favorable signal-to-noise characteristics and the very low background response. Such low background current was attributed to the low (O.OV) operating potential. In addition, no apparent noise contribution from the connecting cable was observed (despite the 50 foot long solution/instrument distance). Detection limits were thus similar to those of conventional (non-remote) tyrosinase electrodes. Further lowering of the detection limits (down to the low nanomolar level) can be achieved in connection with bioamplification schemes.

The sample/instrument distance (i.e., cable length) had no effect upon the response to phenol or the corresponding noise level. Similar response characteristics were observed using distances of 25, 50 and 100 feet. Indeed, the performance with such cables was similar to that observed (with the same electrode housing) without the cable.

Figure 9A:
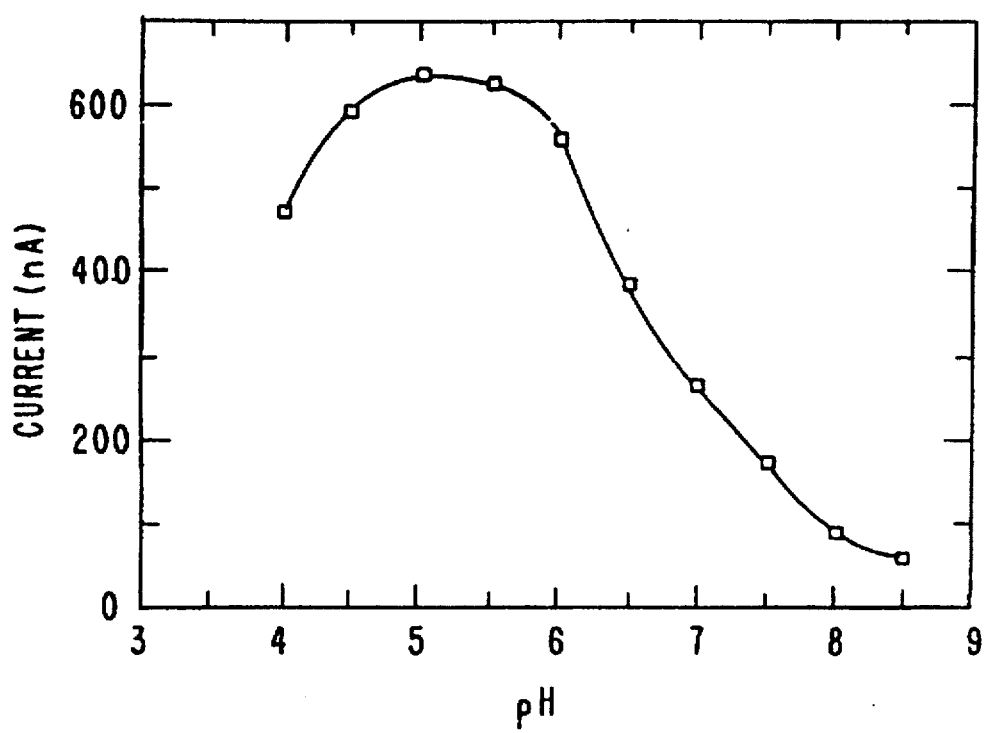
FIG. 9A and 9B show graphs of the influence of pH on the sensor of FIG. 7.
Figure 9B:
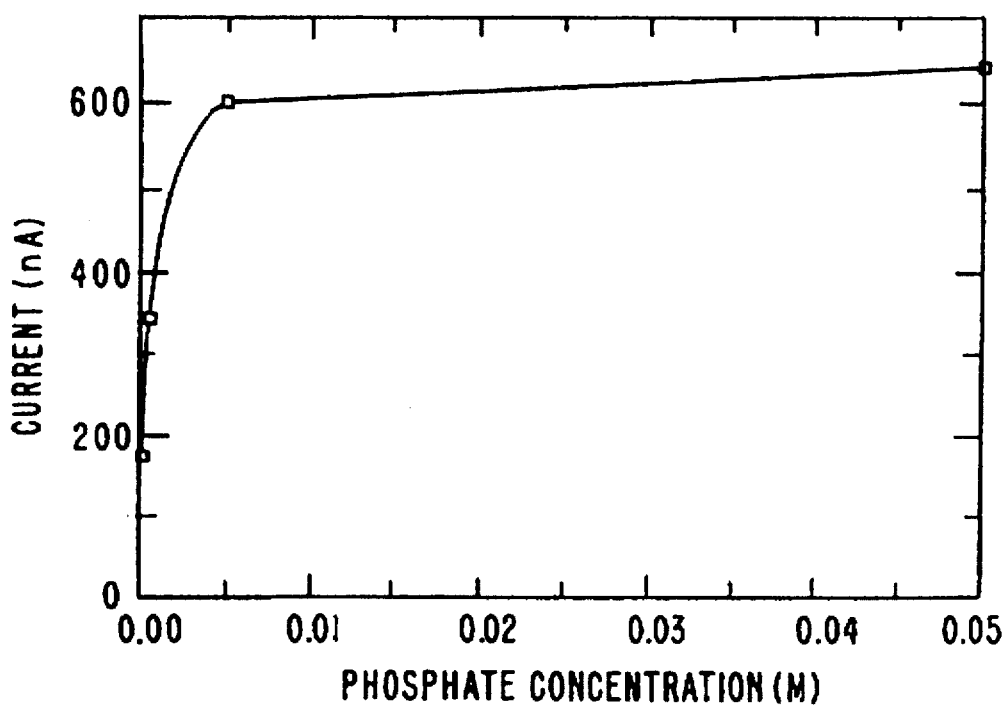

The influence of the pH upon the response of the remote electrode is displayed in FIG. 9(A). High sensitivity was observed over a broad pH range (4.5–6.5), relevant to most natural water samples, with decreased response at higher pH values. Such pH profile reflects the broad pH activity of tyrosinase (see G. Rivas, et al., *Bioelectrochem. Bioenerg.*, 1992, 29, 19). FIG. 9(B) shows the effect of the buffer concentration upon the sensor response. A similar sensitivity was observed between 5 and 50 mM (and at higher levels (not shown)). About 40% and 70% signal losses are observed at 1- and 0 mM buffer, respectively.

Figure 10:
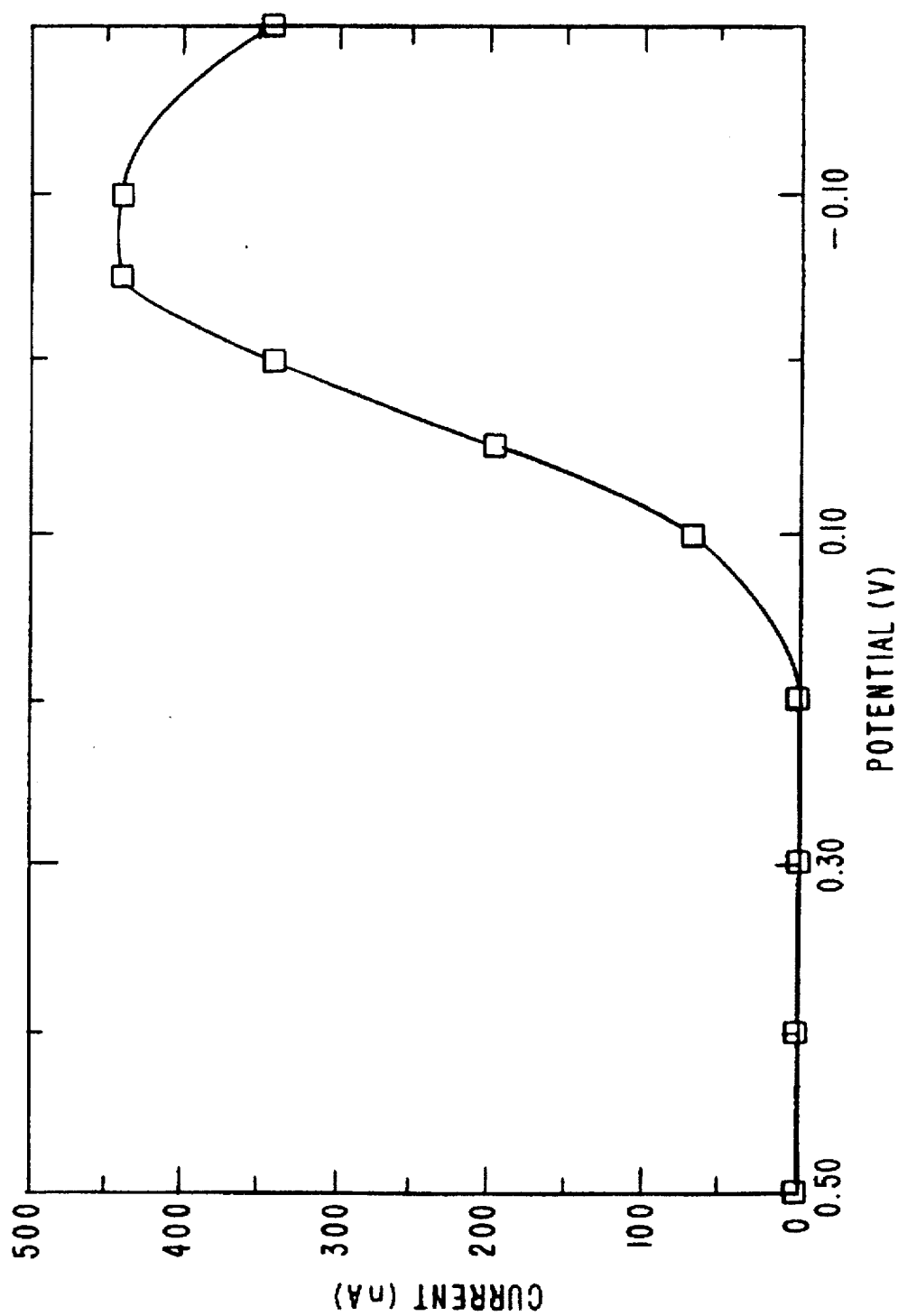
FIG. 10 shows a graph of the dependence of the operating potential upon the FIG. 7 sensor response to phenol.

Minimal dependence on mass transport is another useful property of the tyrosinase-based sensor. For example, only a 15% increase in the $5\times10^{-6}$M phenol response was observed upon stirring the solution (at 1000 rpm), as compared to the response in quiescent media. Kinetic control of the biocatalytic reaction accounts for this behavior, which is attractive for minimizing the effect of fluctuations in the natural convection under remote conditions. FIG. 10 displays the dependence of the operating potential upon the response to $5\times10^{-6}$M phenol. Reductive detection of the liberated quinone product started at +0.2V, rose sharply up to –0.05V, and decreased above –0.1V. Potential steps to 0.0V were employed in all subsequent work, as a compromise between sensitivity and selectivity. Such operating potential eliminated possible contributions from coexisting electroactive constituents.

Figure 11A:
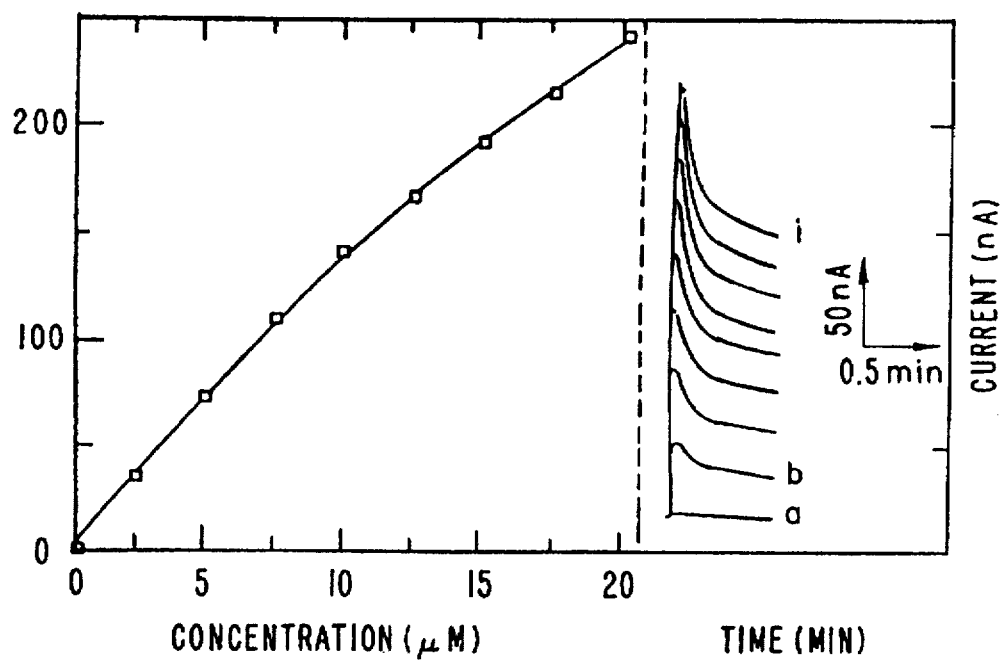
FIG. 11 shows graphs of the FIG. 7 sensor response to untreated river water (A) and groundwater (B)
Figure 11B:
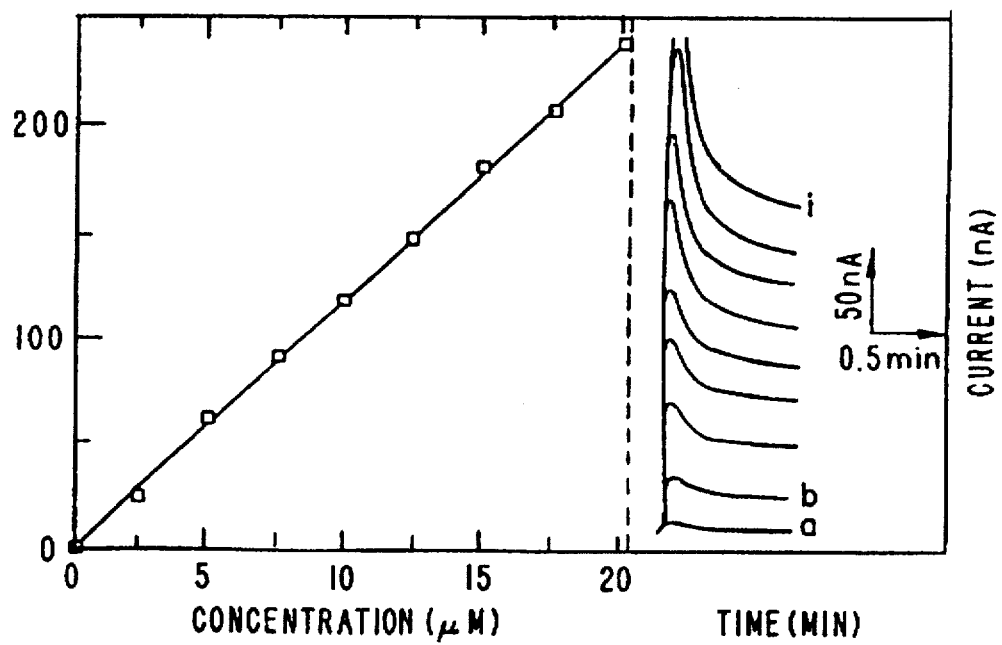

The inherent selectivity and sensitivity of the probe led to convenient quantitation of phenolic substrates in relevant environmental samples. FIG. 11 displays the response to untreated river (A) and groundwater (B) samples containing increasing levels of cresol and phenol, respectively. A favorable response was observed in both samples to these 2.5× $10^{-6}$M concentration changes (b-i). The corresponding background chronamperograms (a) indicated negligible contributions from electroactive matrix constituents. Apparently, the biological recognition, coupled with the low potential operation, allows "fishing out" the target phenolic analytes from complex environmental matrices. High sensitivity was also indicated from the well-defined response and resulting calibration plots. A similar performance was observed in analogous measurements of phenol in river water and cresol in groundwater.

Figure 12A:
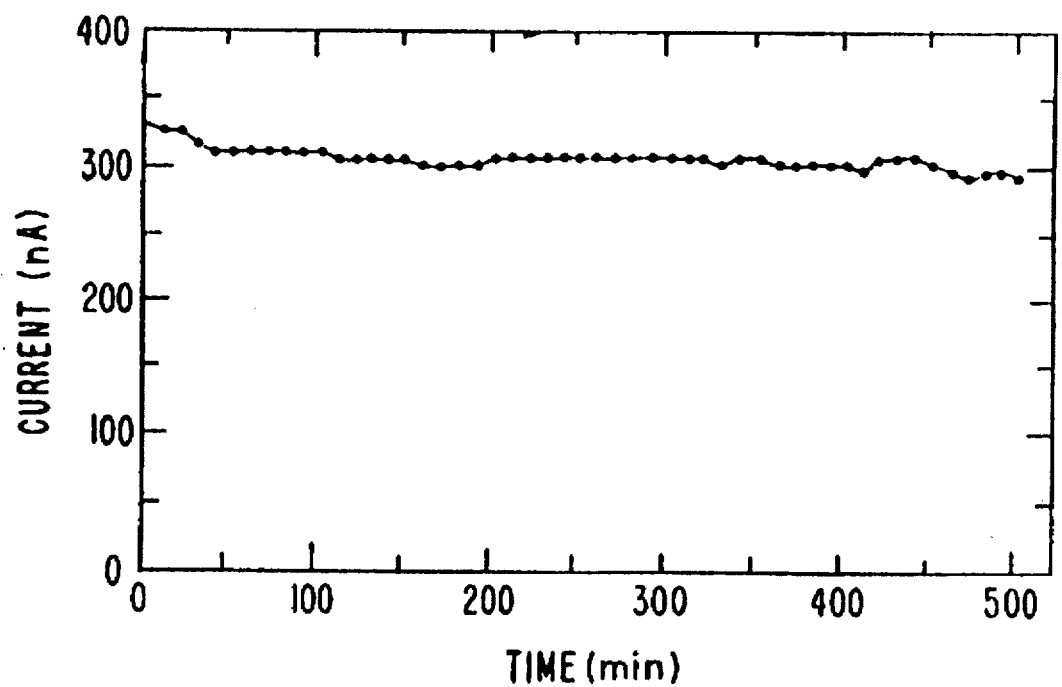
FIG. 12 shows graphs of the response of the FIG. 7 sensor over prolonged period to a constant concentration of phenol (a) and to dynamic changes in phenol concentration (b).
Figure 12B:
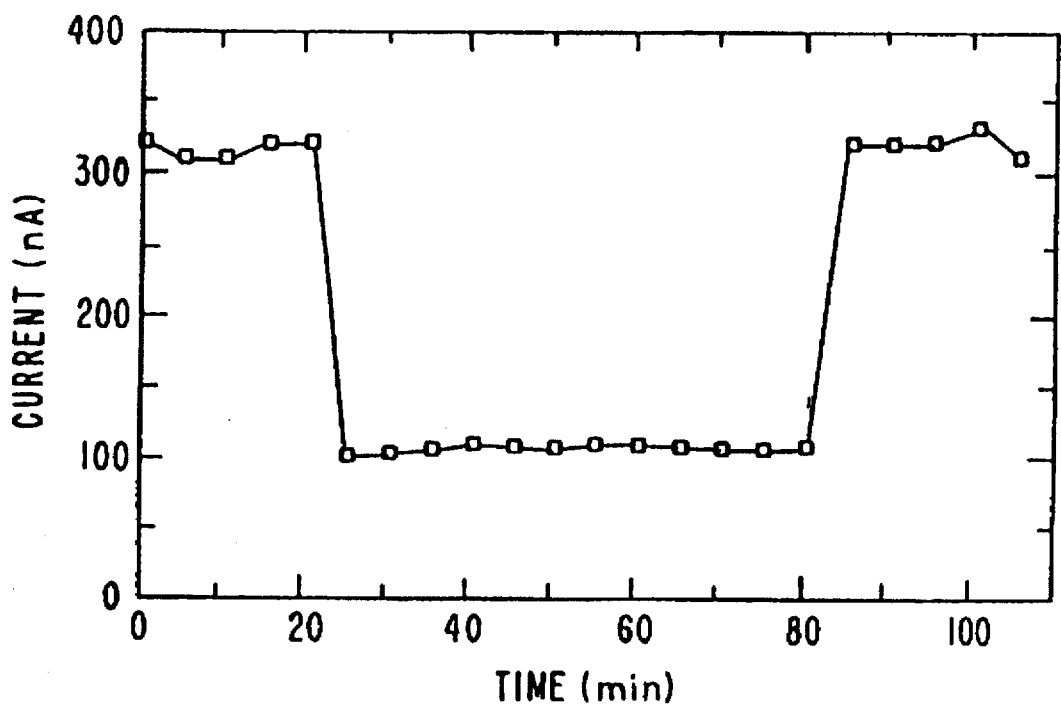

Remote environmental sensors need to rapidly respond to sudden changes in the analyte concentration and offer a highly stable response. A near real-time monitoring was obtained by carrying the measurement at 1 minute intervals (in accordance to the chronamperometric protocol). As indicated from FIG. 12(B), the enzyme probe responds rapidly to dynamic changes in the phenol concentration. No apparent carry over was observed between river water samples spiked with $5 \times 10^{-6}$M and $2 \times 10^{-5}$M phenol. Notice also the reproducibility of the 12 runs at the $5 \times 10^{-6}$M level. The protocol and data of FIG. 12(B) show how pre- and post-field calibrations can be utilized. The long term stability is illustrated in FIG. 12(A) from repetitive chronamperograms (for a river water sample containing $2 \times 10^{-5}$M phenol) recorded at 10 minute intervals over a prolonged (500 min) period. A relative standard deviation of 2.4% was calculated for the 50 runs of this series. Similar stability (rsd=2.6%) was observed for analogous assays of a groundwater sample.

Despite the absence of a protective membrane, no apparent sensor passivation (e.g., surface fouling by matrix constituents) was observed in these experiments. In addition, the biocatalytic activity was maintained over long periods (e.g., ca. 80% after 2 weeks), in accordance with the known stability of tyrosinase (see M. Bonakdar, *Electroanal. Chem.*, 1989, 266, 47; J. Wang, *Analyst*, 1994, 119, 455; L. Campanella, *Analyst*, 1993, 118, 979; F. Ortega, *J. Pharm. Bioomed. Anal.*, 1992, 10, 789; J. Wangsa, *Anal. Chem.*, 1988, 60, 1080). Whenever needed, the probe design permitted easy and fast replacement of the enzyme-electrode tip.

The above examples illustrate the ability to employ enzyme electrodes for monitoring organic compounds at large sample/instrument distances. The remote monitoring capability is coupled to a selective, sensitive and reversible response. Down-hole well monitoring and cone penetrometer insertions can also be made.

The preceding examples can be repeated with similar success by substituting the generically or specifically described reactants and/or operating conditions of this invention for those used in the preceding examples. Some of the discussion of the metal sensor and biosensor is applicable to the other sensor, particularly the connector and housings.

Although the invention has been described in detail with particular reference to these preferred embodiments, other embodiments (e.g. bioelectrodes, modified electrodes) can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. A field environmental analysis apparatus for determining the presence of pollutants in a natural environmental matrix comprising:

a sensor assembly housed within an environmentally sealed connector including multiple electrodes submerged in the natural environmental matrix, one of said electrodes sensitive to the presence of a pollutant;

a battery-powered analytical device;

a cable interconnecting said sensor assembly and said analytical device; and said analytical device including means for applying a periodic voltage to the sensor assembly, means for receiving a response from said sensor assembly, and means for converting, in real time, the measured response to determine the presence of a pollutant.

2. The apparatus of claim 1 wherein said sensor assembly comprises in addition to said pollutant sensitive electrode, a reference electrode and a counter electrode.

3. The apparatus of claim 1 wherein said pollution sensitive electrode is electrochemically reactive with the pollutant.

4. The apparatus of claim 3 wherein the pollution sensitive electrode comprises a metal or carbon and the pollutant comprise a metal.

5. The apparatus of claim 4 wherein the pollution sensitive electrode comprises at least one member selected from the group consisting of carbon and metal.

6. The apparatus of claim 3 wherein the pollution sensitive electrode comprises an enzyme and the pollutant comprise an organic compound.

7. The sensor of claim 6 wherein the electrode comprises tyrosinase.

8. The apparatus of claim 6 wherein the pollutant is a phenolic compound.

9. The apparatus of claim 1 wherein the pollution sensitive electrode comprises at least one member selected from the group consisting of fibers and arrays.

10. The apparatus of claim 1 wherein said cable comprises multiple individually insulated metallic conductors, at least one conductor for each electrode, a shield disposed around said conductors and an outer insulation sheath.

11. The apparatus of claim 1 wherein said analytical device includes means for cleaning the electrode, means for stripping the electrode of a positive metal, and means for applying a negative voltage to said pollution sensitive electrode to permit the depositing of the metal pollutant thereon.

12. The apparatus of claim 11 wherein said means for cleaning the electrode comprises means for applying a voltage of less than approximately +1.0 V for a period of less than approximately five minutes; said means for stripping metal comprises means for applying a constant oxidation current in the range of approximately 0.1 to 5.0 µA for a period of less than approximately five minutes; and said means for collecting said metal pollutant samples comprises means for applying a voltage between approximately −0.1 and −1.0 V for a period of less than approximately five minutes.

13. The apparatus of claim 12 wherein the combined collecting, stripping and cleaning functions are accomplished in less than approximately 5 minutes.

14. The apparatus of claim 1 wherein the sensor performs continuous, timed monitoring and analysis.

15. The apparatus of claim 14 wherein the sensor performs at least approximately 15 runs/analyses per hour.

16. A method for on-site in situ environmental analysis utilizing potentiometric stripping analysis to determine the presence of pollutants comprising the steps of:

temporarily depositing a sensor assembly housed within an environmentally sealed connector including multiple electrodes, one of which is a pollution sensitive electrode, into a natural environmental matrix at a depth below the surface of the matrix;

locating a portable, battery-powered environmental analytical device on the surface of the matrix;

connecting the electrodes of the sensor assembly through a multiple conductor cable to the analytical device;

periodically applying a low-voltage signal from the analytical device to the sensor assembly;

measuring the response to said signal from the electrode assembly; and continuously converting, in real time, the measured response to determine the presence of a pollutant.

17. The method of claim 16 for determining the presence of metal pollutants wherein the step of applying a voltage potential includes the steps of:

cleaning the electrode for a period of less than approximately five minutes at a voltage of less than approximately +1.0 V depositing a metal constituent in the matrix by applying a voltage of between approximately −0.1 and −1.0 V for a period of less than approximately five minutes; and stripping the deposited metal constituent by applying a constant oxidation current, in the range of approximately 0.1 to 5.0 µA, for a period of less than approximately five minutes.

18. The method of claim 17 wherein the cleaning, collecting, and stripping steps are repeated at least approximately fifteen times per hour.

19. The method of claim 16 additionally comprising the steps of connecting at least one of the multiple conductors to each sensor and insulating the signals on the conductors from ambient electrical noise.

20. The method of claim 16 for determining the presence of organic compound pollutants and comprising the additional steps of:

applying an enzyme contained in a paste to the pollutant sensitive electrode;

periodically applying a voltage potential; and measuring the resultant current transients to thereby measure quinone products of environmentally relevant phenolic substrates.

21. The method of claim 16 including insulation of the current transient response of the sensor from environmental electrical noise.

22. The method of claim 16 wherein the applied voltage is changed in steps from approximately +0.2 V to −0.1 V.

23. The method of claim 22 wherein the step of applying the voltage is performed at intervals of approximately 15 minutes or less.

24. The method of claim 16 wherein the steps of periodically applying a low voltage signal and measuring the response is continuous.

* * * * *